US011478412B2

(12) United States Patent
Kadir et al.

(10) Patent No.: US 11,478,412 B2
(45) Date of Patent: Oct. 25, 2022

(54) HAIR MODIFICATION COMPOSITION AND METHOD THEREFOR

(71) Applicant: Lubrizol Advanced Materials, Inc., Cleveland, OH (US)

(72) Inventors: Murat Kadir, Broadview Heights, OH (US); Wing K. Li, East Brunswick, NJ (US); Carole A. Lepilleur, Akron, OH (US); Jean H. Xavier, Plainsboro, NJ (US); Narjis A. Askar, Saint Charles, IL (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 17/046,940

(22) PCT Filed: Apr. 11, 2019

(86) PCT No.: PCT/US2019/026868
§ 371 (c)(1),
(2) Date: Oct. 12, 2020

(87) PCT Pub. No.: WO2019/200027
PCT Pub. Date: Oct. 17, 2019

(65) Prior Publication Data
US 2021/0154120 A1   May 27, 2021

Related U.S. Application Data

(60) Provisional application No. 62/656,665, filed on Apr. 12, 2018.

(51) Int. Cl.
| | |
|---|---|
| *A61Q 5/04* | (2006.01) |
| *A61K 8/49* | (2006.01) |
| *A61K 8/34* | (2006.01) |
| *A61K 8/36* | (2006.01) |
| *A61K 8/362* | (2006.01) |
| *A61K 8/365* | (2006.01) |
| *A61K 8/92* | (2006.01) |
| *A61Q 5/00* | (2006.01) |
| *A61Q 5/12* | (2006.01) |

(52) U.S. Cl.
CPC ............ *A61K 8/4973* (2013.01); *A61K 8/345* (2013.01); *A61K 8/361* (2013.01); *A61K 8/362* (2013.01); *A61K 8/365* (2013.01); *A61K 8/92* (2013.01); *A61Q 5/002* (2013.01); *A61Q 5/04* (2013.01); *A61Q 5/12* (2013.01); *A61K 2800/30* (2013.01); *A61K 2800/413* (2013.01); *A61K 2800/48* (2013.01); *A61K 2800/5426* (2013.01); *A61K 2800/624* (2013.01); *A61K 2800/805* (2013.01); *A61K 2800/882* (2013.01)

(58) Field of Classification Search
None
See application file for complete search history.

(56) References Cited

U.S. PATENT DOCUMENTS

| | | |
|---|---|---|
| 2,773,070 A | 12/1956 | Lichtenwalter et al. |
| 2,798,053 A | 7/1957 | Brown |
| 2,826,551 A | 3/1958 | Geen |
| 2,873,282 A | 2/1959 | McClellan |
| 3,657,175 A | 4/1972 | Zimmerman |
| 3,929,678 A | 12/1975 | Laughlin et al. |
| 3,964,500 A | 6/1976 | Drakoff |
| 3,966,903 A | 6/1976 | Torii et al. |
| 4,152,416 A | 5/1979 | Marra et al. |
| 4,364,837 A | 12/1982 | Pader |
| 4,384,096 A | 5/1983 | Sonnabend |
| 4,464,524 A | 8/1984 | Karickhoff |
| 4,509,949 A | 4/1985 | Huang et al. |
| 4,565,647 A | 1/1986 | Llenado |
| 4,654,207 A | 3/1987 | Preston |
| 4,801,671 A | 1/1989 | Shay et al. |
| 5,019,376 A | 5/1991 | Uick |
| 5,087,445 A | 2/1992 | Haffey et al. |
| 5,104,646 A | 4/1992 | Bolich, Jr. et al. |
| 5,106,609 A | 4/1992 | Bolich, Jr. et al. |
| 5,136,063 A | 8/1992 | O'Lenick et al. |
| 5,180,843 A | 1/1993 | O'Lenick et al. |
| 5,292,843 A | 3/1994 | Jenkins et al. |
| RE34,584 E | 4/1994 | Grote |
| 5,384,114 A | 1/1995 | Dowell et al. |
| 5,720,964 A | 2/1998 | Murray |
| 5,858,948 A | 1/1999 | Ghosh et al. |
| 6,573,375 B2 | 6/2003 | Polovsky et al. |
| 6,727,357 B2 | 4/2004 | Polovsky et al. |
| 7,205,271 B2 | 4/2007 | Drzewinski et al. |
| 7,378,479 B2 | 5/2008 | Tamareselvy et al. |
| 8,153,109 B2 | 4/2012 | Takahashi et al. |
| (Continued) | | |

FOREIGN PATENT DOCUMENTS

| | | |
|---|---|---|
| EP | 0334586 | 9/1989 |
| EP | 0277428 | 3/1991 |
| (Continued) | | |

*Primary Examiner* — Jyothsna A Venkat
(74) *Attorney, Agent, or Firm* — Thoburn Dunlap

(57) ABSTRACT

A composition and a process for modifying hair are disclosed. The process includes coating hair fibers with a composition comprising propylene carbonate and a glycol selected from at least one of propylene glycol, 1,3-propane diol, dipropylene glycol, tripropylene glycol, and mixtures thereof and contacting the coated hair with a heating appliance at a temperature of at least 150° C. for a sufficient time to modify the hair fibers.

4 Claims, 1 Drawing Sheet

(56) References Cited

U.S. PATENT DOCUMENTS

| | | |
|---|---|---|
| 9,872,824 B2 | 1/2018 | Kadir et al. |
| 10,832,235 B2 | 11/2020 | Batlle |
| 2008/0075681 A1 | 3/2008 | Cassier et al. |
| 2012/0138079 A1 | 6/2012 | Knight et al. |
| 2013/0017239 A1 | 1/2013 | Viladot Petit et al. |
| 2016/0296449 A1* | 10/2016 | Kadir .................. A61Q 5/06 |
| 2019/0387856 A1* | 12/2019 | Nowak .................. A45D 6/00 |

FOREIGN PATENT DOCUMENTS

| | | |
|---|---|---|
| EP | 0403238 | 3/1992 |
| EP | 0486135 | 9/1992 |
| EP | 0582152 | 3/1998 |
| GB | 849433 | 9/1960 |
| WO | 9311103 | 6/1993 |
| WO | 9323009 | 11/1993 |
| WO | 9921530 | 5/1999 |
| WO | 20130125053 | 8/2013 |
| WO | 20130144263 | 10/2013 |
| WO | 20150094760 | 6/2015 |
| WO | 2017/096005 A1 | 6/2017 |

\* cited by examiner

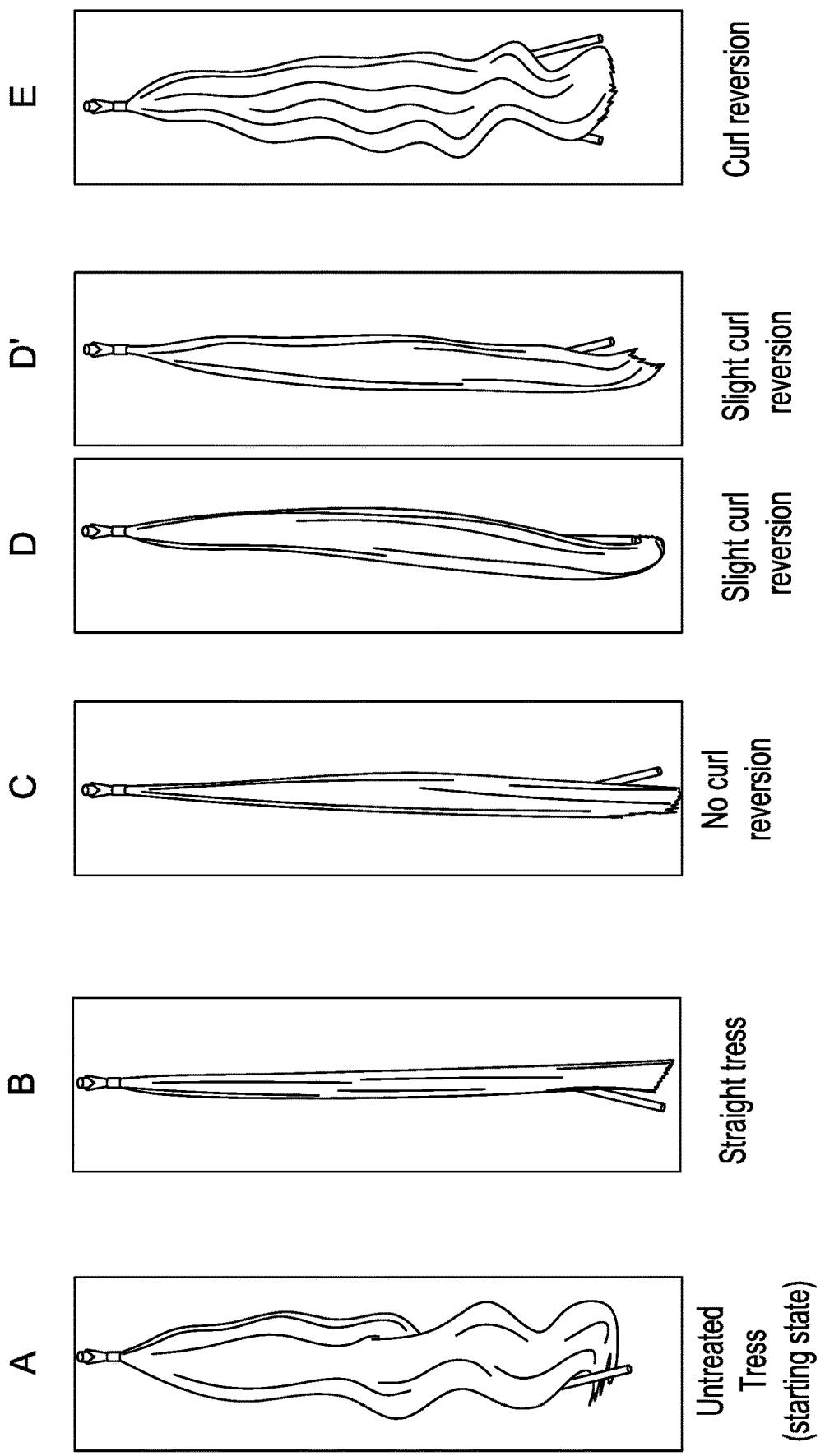

HAIR MODIFICATION COMPOSITION AND METHOD THEREFOR

CROSS REFERENCE TO RELATED APPLICATION

This application claims priority from PCT Application Serial No. PCT/US2019/02868 filed on Apr. 11, 2019, which claims the benefit of U.S. Provisional Application No. 62/656,665 filed on Apr. 12, 2018, both of which are incorporated in their entirety by reference herein.

BACKGROUND

The present technology relates to a hair care composition for modifying hair fibers. The composition comprises a particular combination of propylene carbonate and at least one glycol selected from propylene glycol, 1,2-propane diol, dipropylene glycol, tripropylene glycol, and mixtures thereof. The present technology is utilizable for straightening, smoothing, conditioning and reparing hair fibers by coating the hair with the disclosed composition followed by contacting the coated hair fibers with a heating appliance to modify the hair.

Various methods are available for semi-permanent and permanent modification of hair which can maintain the hair in a modified state for several washes. Many of the permanent treatment methods make use of harsh chemicals which can be hazardous to those performing and receiving the treatment or which give off unpleasant odors. Some of these methods are based on cleavage of the cystine disulfide covalent bonds that are present in keratin. In one method, the disulfide bonds are first broken with a reducing agent. Then a fixative, such as hydrogen peroxide, is applied while the hair is under tension to reconstitute the disulfide bonds in a different arrangement. The peroxide can cause damage to the hair and scalp. Other methods use a hydroxide base which replaces the disulfide bonds ($-CH_2-S-S-CH_2-$) with lanthionine bonds ($-CH_2-S-CH_2-$) in a two-stage process using a hydroxide ion in the first step and a thiol group in the second. The hydroxide is used at fairly high concentrations and can cause scalp burning, and irritation or damage of the eyes and nose. Thiols leave the hair with an unpleasant odor and can lead to degradation of the hair fibers.

Semi-permanent methods use a cross-linking agent to form bonds while the hair is heated. Formaldehyde, for example, is used in many commercial modifying products, either as an ingredient of the composition or as a reaction product that is formed on heating of the hair. However, it can cause allergic reactions to the skin, eyes and lungs, can cause severe damage to the eyes, and poses other health risks. The use of formaldehyde in hair compositions has been discouraged or banned in some countries but it remains in widespread use, due to its effectiveness. Relaxing compositions including a denaturing agent such as urea have also been proposed. However, while urea is less caustic than a hydroxide-based composition, it can decompose to ammonia and poisonous isocyanic acid at the high temperatures used for thermal hair modifying.

There has been a growing trend in the market for semi-permanent curl reduction and/and or shape modification of the hair with minimum hair damage. These products affect the style configuration of hair with discernible curl reduction and ease of styling attributes including shine, luster, smoothness, volume reduction, and feel of hair.

U.S. Pat. No. 3,966,903 discloses a hair-waving (curling) composition containing (A) a hair waving agent selected from sulfite and bisulfite containing compounds and (B) at least one wave accelerating agent including an alkylene carbonate such as propylene carbonate. The wave accelerating agent is said to introduce the sulfite or bisulfite waving agent into the hair cuticle and allowing the waving agent to penetrate the hair keratin. As illustrated in Example 1, the disclosed waving method includes winding the hair to be treated around a curling implement (i.e., glass rod) placing the wound hair in the disclosed hair waving composition, and then rinsing the teated hair with water. No heating step is disclosed.

Japanese Published Patent Application JP 2007-176796 concerns a composition and method for straightening frizzy hair. The composition contains (a) an inositol phosphoric acid derivative as the active hair straightening compound, and (b) an ethanol solvent. Numerous hair penetration enhancing agents including alkylene carbonates (e.g., propylene carbonate) and aliphatic polyhydric alcohols containing 1 to 8 carbon atoms (e.g., propylene glycol, 1,3-propane diol, dipropylene glycol) optionally can be included in the composition. The process includes an optional heating step where the hair is immersed into the pre-heated hair straightening agent, or the pre-heated hair straightening agent is applied to the hair, or only the hair may be heated before the hair is immersed into the straightening agent or the straightening agent is applied to the heated hair. The disclosed heating technique includes a hair iron. The temperature for all treatment methods ranges from 30 to 160° C.

U.S. Published Patent Application 2008/0075681 discloses a composition and process for permanent hair shaping. The composition includes (a) a N-alkyl-2-mercaptoacetamide hair shaping agent, (b) a hair swelling agent and penetration aid, and (c) water. The hair swelling and penetration aid is selected from a list of compounds including trimethylene glycol (1,3-propane diol), propylene carbonate. A wide variety of optional additional ingredients such as hair fixative polymers and polymer plasticizers can be formulated into the disclosed composition. A disclosed polymeric plasticizing agent is propylene glycol. The disclosed hair shaping process includes (i) putting the hair in a desired shape; (ii) before and/or after the hair is put into a desired shape, applying the disclosed hair shaping compositon to the hair; (iii) rinsing the hair with water or applying an intermediate treatment agent containing a betaine, citric acid, latic acid and/or glycolic acid; (iv) oxidatively post-treating the hair; and (v) rinsing the hair with water, followed by dyeing.

U.S. Published Patent Application 2008/0118455 relates to storage stable permanent hair waving compositions containing (a) a cyclic mercapto containing compound (e.g., 2-mercapto-lactone, 2-mercapto-lactam) in (b) an alkylene carbonate diluent (e.g., ethylene carbonate, propylene carbonate). The alkylene carbonate is said to stabilize the cyclic mercapto compound against degradation. Optionally, the permanent hair waving composition may contain other additives including polyhydric alcohols such as propylene glycol and dipropylene glycol among other alcohols. There is no general disclosure of a treatment method other than the waving efficiency test method (Kirby method) disclosed in the examples. A test hair piece was fixed on a Kirby test apparatus followed by treatment of the test piece with the exemplified hair waving compositions at 30° C. for 10 minutes, followed by rinsing.

French Published Patent Application FR 2 978 038 relates to a process for dyeing keratinous fibers comprising (i) a first step of applying to said keratinous fibers a composition comprising one or more ionic salt liquids, then (ii) a second step of heat treatment of the keratin fibers, and then (iii) a third step of application to the keratinous fibers of one or more cosmetic compositions comprising one or more oxidation dyes and/or one or more direct dyes. The ionic liquid salts used according to the disclosure have a mineral or organic cation preferably chosen from imidazolium, pyrazolium, pyridinium, pyrimidinium, tetraalkyl ($C_1$-$C_6$) phosphonium, tetra ($C_1$-$C_6$) alkyl ammonium cations, guanidinium, cholinium, pyrrolidinium, uronium, thiouronium and isothiouronium. The liquid ionic composition optionally includes a solvent selected from a myriad of organic compounds including propylene carbonate and propylene glycol. During step b), the keratinous fibers are heated at a temperature ranging from 50 to 200° C. The heating can be carried out by any conventional heating means, such as hair dryer, helmet, hot iron such as straighteners, curling irons, cakes, or wavers. The heating step can be performed one or more times.

International Published Patent Application WO 2013/125053 discloses a hair dyeing composition and process for dyeing keratin fibers. The composition composition contains (a) one or more natural hair dyes, and (b) a myriad of optional components including organic solvents which are liquid at 25° C. and at atmospheric pressure. Disclosed organic solvents include $C_3$-$C_{10}$ polyols and alkylene carbonates having a Hansen solubility parameter (δH) of less than 15 $MPa^{1/2}$ at 25° C. In addition, the composition may include at least one organic solvent having a different Hansen solubility parameter (OH) than those defined in the disclosure (e.g., propylene glycol).

The hair dyeing process includes (i) applying the disclosed hair dyeing composition onto the keratin fibers to be dyed; (ii) placing the treated keratin fibers into an occlusive space; and (iii) heating the treated fibers in the occlusive space to a temperature ranging from 50 to 250° C. The so-called occlusive space may be formed by coating the treated keratin fibers with at least one coating means including ridged or flexible films or sheets. The heating step is accomplished by hot air, hot steam, high frequency induction, microwave, infrared, laser, and flash lamp means. In one embodiment a mechanical tension by means of a curler, roller, clip, plate or iron may be applied to the treated keratin fibers to provide a desired hair style.

International Published Patent Application WO 2013/144263 relates to a cosmetic composition and process for treating human keratin fibers. The disclosed composition contains (a) one or more non-silicone fatty substances that is present in the composition in an amount greater than 40 wt. % (based on the amount of the total composition), (b) a particulate inorganic thickener, and optionally (c) one or more organic solvents selected from $C_1$-$C_4$ alcohols; polyols such as propylene glycol and polyol ethers; and propylene carbonate. The process according to the disclosure includes a step of heating the hair to a temperature ranging from 60 to 250° C. by means of a heating iron after the application of the cosmetic composition.

International Published Patent Application WO 2015/094760 describes a composition and method for shaping keratin fibers using a carbonate ester formulation. The disclosed formulation contains (a) a carbonate ester including 4-methyl-1,3-dioxolan-2-one (propylene carbonate), (b) a sugar or reducing sugar, and (c) a cosmetically acceptable carrier. Disclosed cosmetically acceptable carriers include aqueous and aqueous-alcoholic systems. Disclosed alcohols include ethanol, isopropanol, propanol, and their mixtures.

The method according to the disclosure involves (i) applying the shaping composition to the hair; (ii) permitting the shaping composition to remain on the hair for a desired amount of time; and (iii) mechanically shaping the treated hair at a temperature of 50 to 250° C. with a heated hair appliance to a desired configuration.

U.S. Published Patent Application 2016/0367462 relates to a method for the cosmetic treatment of keratin materials by providing a liquid ionic composition which enables cosmetically active ingredients to better penetrate the keratin. The method includes (i) application of a composition containing a first, water-soluble ionic liquid $A^+X^-$ including an organic cation $A^+$, and ii) application of a composition comprising a water-soluble salt $B^-Y^+$ including an anion $B^-$, the anion $B^-$ is such that it forms a second, hydrophobic ionic liquid $A^+B^-$ by ion exchange with the first ionic liquid $A^+X^-$. Disclosed cations $A^+$ are selected from imidazolium, pyrazolium, pyridinium, pyrimidinium, tetra($C_1$-$C_6$)alkylphosphonium, tetra($C_1$-$C_6$)alkylammonium, guanidinium, cholinium, pyrrolidinium, uronium, thiouronium and isothiouronium cations. The liquid ionic composition optionally includes a solvent selected from a myriad of organic compounds including propylene carbonate and propylene glycol. When applied to the hair the method may include a heat treatment step at a temperature ranging from 150 to 250° C.

U.S. Pat. No. 9,872,824 discloses a composition and method for semi-permenant hair straightening. The composition discloses an alkylene carbonate hair straightening composition including ethylene carbonate and/or propylene carbonate. The composition may further include a solvent or diluent in which the alkylene carbonate is soluble or dispersible. Disclosed solvents are water, $C_1$-$C_{10}$ aliphatic and aromatic alcohols, including diols and triols, such as glycols (e.g., ethylene glycol, propylene glycol, and glycerine), polyols, and mixtures thereof. The patent indicates that the active alkylene carbonate hair straightening agent can be present in the composition in an amount ranging from 5 to 95 wt. %, based on the weight of the total composition. However, there is no specific disclosure on the amount of solvent or diluent that is contained in the disclosed formulations. The disclosed hair treatment method entails coating the hair fibers to be straightened with the hair treatment composition followed by flat iron straightening at a temperature of at least 150° C.

While hair tresses treated with ethylene carbonate formulations (Table 3) and formulations containing 90/10 to 50/50 (wt./wt.) combinations of ethylene carbonate/propylene carbonate (Table 4) maintain the straightening effect following flat iron straightening at elevated temperatures after numberous wash cycles, hair tresses treated with propylene carbonate formulations followed by similar flat iron exposures became curly even after 3 wash cycles (Table 5).

None of the foregoing documents describe or contemplate a hair modification composition and method wherein the composition is devoid of harsh chemical reducing or oxidizing agents that can damage the hair and scalp and produce maliferous odors.

Surprisingly, the present inventors have discovered that a specific combination of propylene carbonate and a glycol selected from propylene glycol, 1,3-propane diol, dipropylene glycol, tripropylene glycol, and mixtures thereof when applied to the hair followed by shaping with a heating appliance at a temperature of at least 150° C. the treated hair is able to maintain a desired configuration after multiple wash cycles.

BRIEF DESCRIPTION

In accordance with one aspect of an exemplary embodiment of the present technology, a composition and process for modifying hair is disclosed. The hair modifying composition comprises:

a) propylene carbonate;

b) a glycol selected from at least one of propylene glycol, 1,3-propane diol, dipropylene glycol, tripropylene glycol, and mixtures thereof; and c) a cosmetically acceptable carrier;

wherein the amount of the propylene carbonate component a)+the glycol component b) ranges from about 16 to about 35 wt. %, based on the total wt. of the composition; and wherein the wt. ratio of the propylene carbonate component/the glycol component in the composition ranges from about 0.3 to about 3.5.

The hair modifying process includes coating hair (keratin) fibers with the hair modifying composition and subjecting the coated hair fibers to a temperature of at least 150° C. for sufficient time to modify the keratin fibers into a desired configuration.

BRIEF DESCRIPTION OF THE DRAWINGS

FIG. 1 depicts images of hair tresses of Brazilian Type III hair in various shape configurations reported in Tables 1, 2, 3 and 4.

Hair tress A is untreated hair in the natural state.

Hair tress B was treated by a composition and process of the present technology. The illustrated tress was not subjected to a wash cycle.

Hair tress C was treated by a composition and process of the present technology. The illustrated tress was subjected to 3 wash cycles following the treatment process.

Hair tresses D and D' were treated by a comparative composition not of the present technology. The illustrated tresses were subjected to 3 wash cycles following the treatment process.

Hair tress E was treated by a comparative composition not of the present technology. The illustrated tress was subjected to 3 wash cycles.

DETAILED DESCRIPTION

In all aspects of the disclosed technology all percentages are calculated by the weight of the total composition. All ratios are expressed as weight ratios. All numerical ranges of amounts are inclusive and combinable unless otherwise specified.

The term "cosmetically acceptable" means that the compositions, formulations, or components described for the disclosed technology are suitable for contact with human keratinous tissue without toxicity, incompatability, instability, allergic response. All compositions, formulations, components and ingredients described herein have the purpose of being directly applied to keratinous tissue are limited to those being cosmetically acceptable.

The term "substantially free" means less than 1 wt. %, or less than 0.1 wt. %, or less than 0.01 wt. % of a specified ingredient or component The term "free" means or 0 wt. % of a specified ingredient or component.

While overlapping weight ranges for the various components and ingredients that can be contained in the disclosed compositions have been expressed for selected embodiments and aspects of the disclosed technology, the amount of each component in the disclosed compositions is selected from its disclosed range such that the sum of all components or ingredients in the composition will total 100 weight percent. The amounts employed will vary with the purpose and character of the desired product and can be readily determined by one skilled in the art.

As disclosed herein the hair care compositions contain various conventional additives and adjuvants known in the art, some of which can serve more than one function. For example, a particular component can be listed herein as an emollient but can also function as an emulsifier, humectant, and the like.

The hair care compositions of the disclosed technology may suitably comprise, consist essentially of, or consist of, the components, elements, and process delineations described herein. The disclosed technology illustratively disclosed herein suitably may be practiced in the absence of any element which is not specifically disclosed herein.

Embodiments and aspects described herein may be combinable with other embodiments and/or aspects despite not being expressly exemplified in combination.

Aspects of an exemplary embodiment of the disclosed technology relate to a hair modifying composition and method of use. In one embodiment, an exemplary composition comprises, consists essentially of, or consists of: a) propylene carbonate (4-methyl-1,3-dioxolan-2-one) in combination with a glycol selected from propylene glycol (1,2-propane diol), 1,3-propane diol, dipropylene glycol, tripropylene glycol, and mixtures thereof, and c) a cosmetically suitable carrier. The total amount of propylene carbonate component and the glycol component in the composition ranges from about 16 to about 35 wt. %, or from about 17 to about 30 wt. %, or from about 18 to about 25 wt. %, based on the total weight of the composition. The weight ratio of the propylene carbonate component/the glycol component ranges from about 0.3 to about 3.5, or from about 0.5 to about 3.5, or from about 0.6 to about 3, or from about 0.7 to about 2.5, or from about 0.75 to about 2.

In one embodiment, an exemplary composition comprises, consists essentially of, or consists of: a) propylene carbonate in combination with a glycol selected from propylene glycol, 1,3-propane diol, and mixtures thereof, and c) a cosmetically suitable carrier. The total amount of propylene carbonate component and the glycol component in the composition ranges from about 16 to about 35 wt. %, or from about 17 to about 30 wt. %, or from about 18 to about 25 wt. %, based on the total weight of the composition. The weight ratio of the propylene carbonate component/the glycol component ranges from about 0.3 to about 3.5, or from 0.5 to about 3.5, or from about 0.6 to about 3, or from about 0.7 to about 2.5, or from about 0.75 to about 2.

In one embodiment, an exemplary composition comprises, consists essentially of, or consists of: a) propylene carbonate in combination with a glycol selected from propylene glycol, 1,3-propane diol, and mixtures thereof, and c) a cosmetically suitable carrier. The total amount of propylene carbonate component and the glycol component in the composition ranges from about 16 to about 35 wt. %, or from about 17 to about 30 wt. %, or from about 18 to about 25 wt. %, based on the total weight of the composition. The weight ratio of the propylene carbonate component/the glycol component ranges from about 0.3 to about 3.5, or from about 0.5 to about 3.5, or from about 0.6 to about 3, or from about 0.7 to about 2.5, or from about 0.75 to about 2.

In one embodiment, an exemplary composition comprises, consists essentially of, or consists of: a) propylene carbonate in combination with b) propylene glycol, and c) a cosmetically suitable carrier. The total amount of propylene carbonate component and the propylene glycol component in the composition ranges from about 16 to about 35 wt. %, or from about 17 to about 30 wt. %, or from about 18 to about 25 wt. %, based on the total weight of the composition. The weight ratio of the propylene carbonate component/the propylene glycol component ranges from about 0.3 to about 3.5, or from about 0.5 to about 3.5, or from about 0.6 to about 3, or from about 0.7 to about 2.5, or from about 0.75 to about 2.

In one embodiment, an exemplary composition comprises, consists essentially of, or consists of: a) propylene carbonate in combination with b) 1,3-propane diol, and c) a cosmetically suitable carrier. The total amount of propylene carbonate component and 1,3-propane diol component in the composition ranges from about 16 to about 35 wt. %, or from about 17 to about 30 wt. %, or from about 18 to about 25 wt. %, based on the total weight of the composition. The weight ratio of the propylene carbonate component/the 1,3-diol component ranges from about 0.3 to about 3.5, or from about 0.5 to about 3.5, or from about 0.6 to about 3, or from about 0.7 to about 2.5, or from about 0.75 to about 2.

In one embodiment, the hair care composition is provided in kit form comprising at least two containers. Various of the components of the hair care composition can be separately packaged in two or more containers, and when the contents of the containers are mixed a hair care composition is provided. Upon admixing the contents of the containers, the sum amount of the propylene carbonate component and the glycol component in the hair care composition ranges from about 16 to about 35 wt. %, or from about 17 to about 30 wt. %, or from about 18 to about 25 wt. %, based on the total weight. of the admixed composition; and wherein the weight ratio of the propylene carbonate component/glycol component in said hair care composition ranges from about 0.3 to about 3.5, or from about 0.5 to about 3.5, or from about 0.6 to about 3, or from about 0.75 to about 2.5, or from about 1 to about 2. Optionally, mixing and application instructions for the components and the admixed hair care composition can be provided with the kit. The compositions in the kit may be in the form of a liquid, cream, mousse, gel, paste, spray, or the like.

In another aspect, the disclosed technology concerns a process for modifying keratin fibers, such as human hair. The process includes contacting the keratin fibers with an exemplary composition to coat the fibers, maintaining the keratin-fibers in contact with the composition for sufficient time to effect modifying when the fibers are heated, and optionally drying the fibers to remove at least some of the cosmetically acceptable carrier component. In one embodiment, the keratin fibers, coated with the exemplary composition, are heated with a heating device such as a hand-held hair dryer, a bonnet hair dryer, infrared dryer, and the like at a temperature ranging from about 80 to about 250° C. for a sufficient time.

In another aspect, the process includes contacting the keratin fibers with an exemplary composition of the disclosed technology to coat the fibers, maintaining the keratin fibers in contact with the composition for sufficient time to effect modifying when the fibers are heated (contact time), and optionally drying the fibers to remove at least some of the cosmetically acceptable carrier component. The keratin fibers, coated with the exemplary composition, are contacted with the surface of a heating appliance, such as a flat iron heated to a temperature ranging from about 150 to about 250° C., or from about 175 to about 240° C., or about 200 to about 235° C., or from about 220 to about 230° C., for sufficient time to relax the keratin fibers, e.g., by reaching the glass transition temperature, which can vary, to some degree, depending on the moisture content.

In one aspect, the heated flat iron appliance is pulled through locks of the coated hair to be mechanically waved or straightened. The coated hair locks are placed in the heated flat iron appliance at the root end of the hair and the flat iron is pulled through the length of the hair lock from the root end to the tip to mechanically shape the hair to a desired configuration. In one aspect, the flat iron is pulled through the hair lock from the root end of the hair lock to the tip for at least one pass, or at least 2 passes, or at least 3 passes, or at least 5 passes, or from 1 pass to 10 passes.

In one aspect, the glide speed of the flat iron appliance which is pulled down the length of a lock of coated is at least about 1 cm/sec., or at least about 2 cm/sec, or at least about 3 cm/sec., or at least about 4 cm/sec., or at least about 5 cm/sec., or can range from about 1 to about 10 cm/sec.

In the treatment methods described above, the contact time (also referred to as soak time) is the time interval between coating the keratin fibers and the onset of heating the coated keratin fibers. In one aspect, the soak time is 0 minutes, or at least 1 minute, or at least 5 minutes, or at least 10 minutes or is at least 15 minutes, or at least 20 minutes or at least 25 minutes, or at least 30 minutes, or at least 45 minutes or at least 60 minutes.

The exemplary composition can be utilized on hair to impart an excellent modifying effect by using heat. In one aspect, the treatment method includes first coating the hair with the composition. This may be performed with any suitable applicator, such as a brush, comb, sponge, pad, cloth, fingers e.g., while wearing gloves, to coat the fibers with the composition. The composition is left in contact with the hair for a sufficient contact period (or soak time) for the hair care composition agent to penetrate the fibers, such as previously mentioned. The optimum contacting time may vary, depending on factors such as the concentration of the active hair care agent(s) and the temperature of the heating device used to contact the hair in the heating stage. The composition left in contact with the hair can optionally be applied under heat to improve penetration of the composition into the hair fiber. This can be achieved in various ways including and not limited to a hair drier, infrared lamps, such temperature can be in the range, but not limited to 30° C., 50° C., 55° C., 90° C., 100° C. or 120° C.

After application and an appropriate soak time, heat may be applied with a heating appliance which provides a temperature sufficient to activate the hair care agent of the disclosed technology, such as a temperature of at least 150° C., or at least 190° C., or at least 200° C., or at least 205° C. or at least or about 210° C. and up to 230° C. or up to 225° C., or up to 220° C. The heating device is retained in contact with the hair for sufficient time to get the desired modification, such as hair smoothing, hair waving, hair conditioning, hair repairing, or in case of hair straightening, an increase in length of a hair tress of at least 5%, or at least 10%. The time depends on many factors such as the moisture content of the hair, temperature of the heating device, concentration of the hair care agent and so forth, but is generally at least 10 seconds, or at least 1 or 2 minutes, in total, for each centimeter length of hair. Example heating devices include flat or round irons, microwave generators, sources of infrared radiation, and the like. In the case of flat or round iron, for example, the heating device has at least one surface (which is brought into contact with the fibers) which is raised, e.g., with an electric power source, to a surface temperature of at least 150° C., or at least 190° C., or at least 200° C., or at least 205° C. or at least or about 210° C. and up to 250° C. or up to 230° C., or up to 225° C., or up to 220° C.

Optionally, the hair can be dried to some extent after treatment with the modifying composition and prior to application of heat to raise the temperature of the keratin fibers and/or to avoid substantial release of heat to the environment during the heating stage. For example, partial drying may be achieved by blow drying with a hair dryer, a drying hood at a temperature of about 80° C., by free drying, wiping with a towel, etc. For example, the moisture content of the composition may be reduced to 10 wt. % or less, such as about 2 wt. %, prior to applying heat with the heating appliance. In general, drying is performed to remove solvent while retaining at least a portion, or all, of the applied hair care agent on the hair. For this reason, the hair is not rinsed (e.g., with water or other aqueous solutions) between the application and the heating stages in the exemplary embodiment.

The end of the iron that contacts the hair generally has two flat surfaces. These flat surfaces may be metallic or ceramic. They may be smooth or notched. The application of the iron may be performed by successive touches separated by a few seconds, or by gradual moving or sliding along locks, etc. As mentioned previously, the application of the iron in the exemplary process is performed by continuous movement from the root to the end, optionally, utilizing the glide speeds and number of passes described above.

Without wishing to be bound by any particular theory, it is believed that the hot flat iron softens hard α-keratins and straightens the hair fiber and synergistically, the heat imparted by the flat iron activates a reaction (e.g., a cross-linking or other modification reaction) between propylene/glycol and the amine groups of the hair fibers, possibly resulting in N, N'-disubstituted urea linkages. This results in the fixing of the newly formed shape.

In the treatment methods described above, hair straightening modification generally results in an increase in the average length of the keratin fibers, as measured when a lock of the curly fibers is suspended from a support, of at least 5% or at least 10%, which can be maintained over several hair washing cycles (involving shampooing and drying the hair), such as at least 3, or at least 5, or at least 10 or at least 20 wash cycles. The exemplary process is semi-permanent in that over time, the straightened fibers begin to return to their original, curly state. While the method can be used to form very straight hair, it can also be used in a process in which a semi-permanent wave is created.

Propylene carbonate is particularly suited to the exemplary application as it has low toxicity and does not form toxic byproducts during the heating stage. Propylene carbonate is also reasonalby soluble in water at room temperature (25° C.), up to about 20 wt. %.

Propylene carbonate suitable for use herein is available commercially from various sources including Wego Chemical Group, Great Neck, N.Y. and Seidler Chemical Co., Inc., Newerk, N.J.

U.S. Pat. No. 2,873,282 describes methods for making alkylene carbonates by reacting an alkylene oxide or compound thereof with carbon dioxide. U.S. Pat. No. 2,773,070 describes similar methods.

Propylene glycol, dipropylene glycol and tripropylene glycol suitable for use herein is commercially available from The Dow Chemical Company, Midland, Mich.

1,3-propanediol suitable for use in the present technology is commercially available from Wego Chemical Group, Great Neck, N.Y.

In one aspect biobased or renewably sourced 1,3-propane diol is utilized in the present technology. Biobased 1,3-propane diol is commercially marketed by DuPont Tate & Lyle Bio Products Company, LLC, Loudon Tenn., under the SUSTERRA and ZEMA trademarks.

In one embodiment, the composition (and treatment process described herein) is free or substantially free of formaldehyde. The exemplary method and composition use no formaldehyde either directly, in the composition, or through reaction, during the method, of any sources of formaldehyde. Similarly, the composition and process may be free or substantially free of glyoxylic acid, urea, and derivatives thereof, which can break down to form irritants.

In one embodiment, the composition (and treatment process described herein) is free or substantially free of mercapto or thiol group containing compounds.

In one embodiment, the composition and process are free or substantially free of sulfite and bisulfite containing compounds.

In one embodiment, the composition and process are free or substantially free of hair dyes, including but not limited to dye precursors, direct dyes and oxidative dyes.

In one embodiment, the composition and process are free or substantially free of imidazolium, pyrazolium, pyridinium, pyrimidinium, tetra($C_1$-$C_6$)alkylphosphonium, tetra ($C_1$-$C_6$)alkylammonium, guanidinium, cholinium, pyrrolidinium, uronium, thiouronium and isothiouronium cations.

In one embodiment, the composition and process are free or substantially free of sugars and/or reducing sugars.

In one embodiment, the composition and process are free or substantially free of a photocatalyst.

In one embodiment, the composition and process are free or substantially free of inositol, inositol phosphoric acid and derivatives of inositol phosphoric acid.

In one embodiment, the composition and process are free or substantially free of a particulate inorganic thickener.

In one embodiment, the composition and process are free or substantially free of an alkylene carbonate (including ethylene carbonate, butylene carbonate, glycerol carbonate), other than propylene carbonate.

The semi-permanent hair modifying composition can be provided and dispensed from suitable package forms, such as pressurized and non-pressurized containers, such as cans, bottles, packets, ampoules, jars, tubes, and the like. Spray compositions can be dispensed from finger-actuated pump devices, either as pressurized aerosol sprays, mousses, spritzes, and foams containing propellant, or as non-pressurized, mechanically propelled sprays and foams.

Solvent

The composition can be prepared as water-free or water-based formulations. In addition to the propylene carbonate and selected glycol components present, the composition may include a solvent in which the propylene carbonate and glycol(s) are soluble/dispersible. The solvent may be selected from water, and organic solvent, and combinations of water and an organic solvent. Examples of organic solvents, other than water, include linear and branched alcohols, such as ethanol, propanol, isopropanol, hexanol, and the like; and aromatic alcohols, such as benzyl alcohol, cyclohexanol, and the like. Other examples of non-aqueous solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl carboxylic esters, such as ethyl acetate, amyl acetate, ethyl lactate, and the like, jojoba oil, shark liver oil, and the like.

Some of the foregoing non-aqueous auxiliary solvents or diluents may also serve as conditioners and emulsifiers. For purposes of computing a weight basis in the composition, however, all the liquids listed in this section are considered as solvents/diluents.

Product formulations comprising the composition of the disclosed technology can contain various additives and cosmetic adjuvants, conventionally or popularly included in personal care compositions including, without being limited thereto, acidifying or alkalizing pH adjusting agents (neutralizing agents) and buffering agents; auxiliary fixatives and film formers, such as nonionic, anionic, cationic, or amphoteric polymers of synthetic or natural origin, and the like; auxiliary rheology modifiers, such as viscosity-increasing polymeric natural and derivatized gums, resin thickeners or gellants; additives, such as emulsifiers, emulsion stabilizers, waxes, dispersants, and the like, and viscosity control agents, such as solvents, electrolytes, and the like; auxiliary conditioning agents, such as antistatic agents, synthetic oils, vegetable or animal oils, silicone oils, monomeric or polymeric quaternized ammonium compounds and derivatives thereof, sheen enhancers, moisturizers, emollients, humectants, lubricants, sunscreen agents, and the like; oxidizing agents; reducing agents; surfactants, such as anionic, cationic, nonionic, amphoteric, zwitterionic surfactants, and silicone derivatives thereof; polymer film modifying agents, such as plasticizers, tackifiers, detackifiers, wetting agents, and the like; product stabilizing and finishing agents, such as chelating agents, opacifiers, pearlescing agents, proteinaceous materials and derivatives thereof, vitamins and derivatives thereof, preservatives, fragrances, solubilizers, colorants (temporary or permanent), such as pigments and dyes, UV absorbers, and the like; propellants (water-miscible or water-immiscible), such as fluorinated hydrocarbons, liquid volatile hydrocarbons, compressed gases, and the like; and mixtures thereof.

Additives and adjuvant ingredients, products, or materials, which may be employed with the inventive hair modification composition discussed herein will be referred to by the international nomenclature commonly referred to as INCI name given them in the International Cosmetic Ingredient Dictionary, published by the Personal Care Products Council (formally the Cosmetic, Toiletry, and Fragrance Association), Washington D.C. (hereafter INCI Dictionary), such as can be found in any edition thereof, for example, Volumes 1 and 2, Sixth Edition, (1995) or Volumes 1-3, Seventh and Eighth Editions, (1997, 2000), or by their commonly used chemical names. Numerous commercial suppliers of materials listed by INCI name, trade name or both can be found in the INCI Dictionary and in numerous commercial trade publications, including but not limited to the 2001 McCutcheon's Directories, Volume 1: Emulsifiers & Detergents and Volume 2: Functional Materials, published by McCutcheon's Division, The Manufacturing Confectioner Publishing Co., Glen Rock, N.J. (2001); and 2001 Cosmetic Bench Reference, edition of Cosmetics & Toiletries®, 115 (13), published by Allured Publishing Corporation, Carol Stream, I.L. (2001); the relevant disclosures of each are incorporated herein by reference. Such components and the formulation of compositions are also described in detail in well-known references, such as Cosmetics Science and Technology, First Edition (Sagarin (ed)), published 1957, and Second Edition (Balsam, et al. (eds)), published 1972-74; and The Chemistry and Manufacture of Cosmetics, Second Edition (deNavarre (ed)), published 1975, and Third Edition (Schlossman (ed)), published 2000, both available from Allured Publishing Corporation; Rieger (ed), Harry's Cosmeticology, 8th Edition, Chemical Publishing, Co., Inc., New York, N.Y. (2000); and various formularies available to those skilled in the pharmaceutical arts, such as Remington's Pharmaceutical Sciences, Fourteenth Edition, Mack Publishing Company, Easton, Pa. (1970); the relevant disclosures of each are incorporated herein by reference.

Auxiliary Components
Rheology Modifiers

To provide a composition which adheres well to the hair fibers, the composition can include a rheology modifier which increases the overall viscosity of the composition. The Brookfield viscosity of the composition measured at 20 rpm, when applied to the hair, can be at least 400 mPa·s, or at least 1000 mPa·s, or at least 2000 mPa·s, or at least 3000 mPa·s, and can be up to 10,000 mPa·s.

To increase the viscosity, the composition may include one or more rheology modifiers, which can be synthetic or natural.

Examples include fatty alcohols, such as $C_{10}$-$C_{32}$ alcohols, e.g., $C_{12}$-$C_{22}$ alcohols, natural oils, and polymers of acrylic acid and/or methacrylic acid, such as carbomers. Exemplary natural oils include mineral oils (mainly $C_{15}$-$C_{40}$ linear and branched aliphatic alkanes, with minor amounts of cycloalkanes), which may be sold as paraffinum liquidum.

Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule, wherein in one aspect the substituent is independently selected from $C_1$-4 alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. Nos. 5,087,445; 4,509,949; and 2,798,053.

In one aspect, the AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980, and 996 available from Lubrizol Advanced Materials, Inc. In a further aspect, the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814 which is herein incorporated by reference. Some of the forgoing polymers are designated under INCI nomenclature as Acrylates/$C_{10}$-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc.

In another aspect, the auxiliary rheology modifier can be a crosslinked, linear poly(vinyl amide/acrylic acid) copolymer as disclosed in U.S. Pat. No. 7,205,271, the disclosure of which is herein incorporated by reference.

Another class of synthetic rheology modifiers suitable for use in the composition includes hydrophobically modified ASTs, commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843. In addition, an extensive review of HASE polymers is found in Gregory D. Shay, Chapter 25, "Alkali-Swellable and Alkali-Soluble Thickener Technology A Review", Polymers in Aqueous Media—Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. Commercially available HASE polymers are sold under the trade names, Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer) from Rohm & Haas, and Novethix™ L-10 (INCI Name: Acrylates/Beheneth-25 Methacrylate Copolymer) from Lubrizol Advanced Materials, Inc.

In another embodiment, acid swellable associative polymers can be used with the hydrophobically modified, cationic polymers of the disclosed technology. Such polymers generally have cationic and associative characteristics. These polymers are free radical addition polymers polymerized from a monomer mixture comprising an acid sensitive amino substituted hydrophilic monomer (e.g., dialkylamino alkyl (meth)acrylates or (meth)acrylamides), an associative monomer (defined hereinabove), a lower alkyl (meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth)acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from 0.5 to 6.5. Exemplary acid swellable associative polymers are commercially available under the trade name Structure® Plus (INCI Name: Acrylates/Aminoacrylates/$C_{10}$-$C_{30}$ Alkyl PEG-20 Itaconate) from Akzo Nobel, and Carbopol® Aqua CC (INCI Name: Polyacrylates-1 Crosspolymer) from Lubrizol Advanced Materials, Inc. In one aspect, the acid swellable polymer is a copolymer of one or more $C_1$-$C_5$ alkyl esters of (meth)acrylic acid, $C_1$-$C_4$ dialkylamino $C_1$-$C_6$ alkyl methacrylate, PEG/PPG-30/5 allyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479.

Hydrophobically modified alkoxylated methyl glucosides, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, Glucamate™ VLT and Glucamate™ SSE-20, respectively, are also suitable as rheology modifiers.

Polysaccharides obtained from tree and shrub exudates, such as gum Arabic, gum gahatti, and gum tragacanth, as well as pectin; seaweed extracts, such as alginates and carrageenans (e.g., lambda, kappa, iota, and salts thereof); algae extracts, such as agar; microbial polysaccharides, such as xanthan, gellan, and wellan; cellulose ethers, such as ethylhexylethylcellulose, hydroxybutylmethylcellulose, hydroxyethylmethylcellulose, hydroxypropylmethylcellulose, methylcellulose, carboxymethylcellulose, hydroxyethylcellulose, and hydroxypropylcellulose; polygalactomannans, such as fenugreek gum, cassia gum, locust bean gum, tara gum, and guar gum; starches, such as corn starch, tapioca starch, rice starch, wheat starch, potato starch and sorghum starch can also be employed in the compositions herein as suitable rheology modifiers.

The rheology modifier(s) can be used alone or in combination and may be present in the composition, on an actives basis, at a total concentration of 0.001-50 wt. %, e.g., at least 0.1 wt. %, or at least 1 wt. %, such as up to 20 wt. %, or up to 10 wt. %%, or up to 3 wt. %, based on the total weight of the composition.

Surfactants

The hair care composition may also include one or more surfactants, such as anionic, cationic, amphoteric, and nonionic surfactants, as well as mixtures thereof.

In one aspect of the present technology, suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulfates, alkyl monoglyceryl ether sulfates, alkyl monoglyceride sulfates, alkyl monoglyceride sulfonates, alkyl succinates, alkyl sulfosuccinates, alkyl ether sulfosuccinates, alkyl sulfosuccinamates, alkyl amidosulfosuccinates; alkyl sulfoacetates, alkyl phosphates, alkyl ether phosphates, alkyl ether carboxylates, alkyl amidoethercarboxylates, acyl lactylates, alkyl isethionates, acyl isethionates, carboxylate salts and amino acid derived surfactants such as N-alkyl amino acids, N-acyl amino acids, as well as alkyl peptides. Mixtures of these anionic surfactants are also useful.

In one aspect, the cation moiety of the forgoing surfactants is selected from sodium, potassium, magnesium, ammonium, and alkanolammonium ions such as monoethanolammonium, diethanolammonium triethanolammonium ions, as well as monoisopropylammonium, diisopropylammonium and triisopropylammonium ions. In one embodiment, the alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; the sodium potassium, lithium, magnesium, ammonium, and triethanolammonium salts of lauryl sulfate, coco sulfate, tridecyl sulfate, myristyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium lauroyl isethionate, sodium lauroyl methyl isethionate, sodium $C_{12}$-$C_{14}$ olefin sulfonate, sodium laureth-6 carboxylate, sodium dodecylbenzene sulfonate, triethanolamine monolauryl phosphate, and fatty acid soaps, including the sodium, potassium, ammonium, and triethanolamine salts of a saturated and unsaturated fatty acids containing from about 8 to about 22 carbon atoms.

In one aspect, the amino acid surfactants are selected from a N-acyl amino acid of the formula:

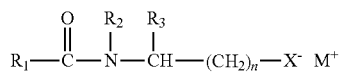

wherein $R_1$ is a saturated or unsaturated, straight or branched alkyl chain containing 7 to 17 carbon atoms, R2 is H or a methyl group, R3 is H, $COO^-M^+$, $CH_2COO^-M^+$ or COOH, n is 0 to 2, X is $COO^-$ or $SO_3^-$ and M independently represents H, sodium, potassium, ammonium or triethanolammonium.

In one aspect, the N-acyl amino acid surfactants represented by the formula immediately above are derived from taurates, glutamates, alanine, alaninates, sacrosinates, aspartates, glycinates, and mixtures thereof.

Representative taurate surfactants conform to the formula:

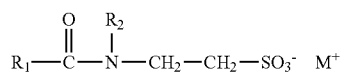

wherein $R_1$ is a saturated or unsaturated, straight or branched alkyl chain containing 7 to 17 carbon atoms in one aspect and 9 to 13 carbon atoms in another aspect, R2 is H or methyl, and M is H, sodium, potassium, ammonium or triethanolammonium.

Non-limiting examples of taurate surfactants are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, and mixtures thereof.

Representative glutamate surfactants conform to the formula:

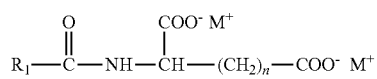

wherein $R_1$ is a saturated or unsaturated, straight or branched alkyl chain containing 7 to 17 carbon atoms in one aspect and 9 to 13 carbon atoms in another aspect, n is 0 to 2, and M independently is H, sodium, potassium, ammonium or triethanolammonium.

Non-limiting examples of glutamate surfactants are di-potassium capryloyl glutamate, di-potassium undecylenoyl glutamate, di-sodium capryloyl glutamate, di-sodium cocoyl glutamate, di-sodium lauroyl glutamate, di-sodium stearoyl glutamate, di-sodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, and mixtures thereof.

Representative alanine and alaninate surfactants conform to the formula:

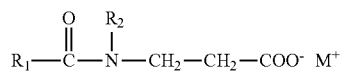

wherein $R_1$ is a saturated or unsaturated, straight or branched alkyl chain containing 7 to 17 carbon atoms in one aspect and 9 to 13 carbon atoms in another aspect, R2 is H or methyl, and M is H, sodium, potassium, ammonium or triethanolammonium.

Non-limiting examples of alanine and alaninate surfactants are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine, sodium myristoyl methyl β-alanine, and mixtures thereof.

Representative glycinate surfactants conform to the formula:

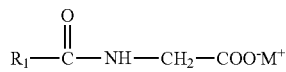

wherein $R_1$ is a saturated or unsaturated, straight or branched alkyl chain containing 7 to 17 carbon atoms in one aspect and 9 to 13 carbon atoms in another aspect, and M is H, sodium, potassium, ammonium or triethanolammonium.

Non-limiting examples of glycinate surfactants are sodium palmitoyl glycinate, sodium lauroyl glycinate, sodium cocoyl glycinate, sodium myristoyl glycinate, potassium lauroyl glycinate, potassium cocoyl glycinate, sodium stearoyl glycinate, and mixtures thereof.

Representative sarcosinate surfactants conform to the formula:

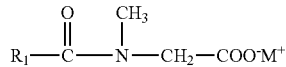

wherein $R_1$ is a saturated or unsaturated, straight or branched alkyl chain containing 7 to 17 carbon atoms in one aspect and 9 to 13 carbon atoms in another aspect, and M is H, sodium, potassium, ammonium or triethanolamine.

Non-limiting examples of sarcosinate surfactants are potassium lauroyl sarcosinate, potassium cocoyl sarcosinate, sodium cocoyl sarcosinate, sodium lauroyl sarcosinate, sodium myristoyl sarcosinate, sodium palmitoyl sarcosinate, and mixtures thereof.

Representative aspartate surfactants conform to the formula:

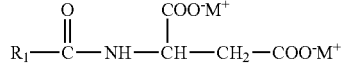

wherein $R_1$ is a saturated or unsaturated, straight or branched alkyl chain containing 7 to 17 carbon atoms in one aspect and 9 to 13 carbon atoms in another aspect, and M independently is H, sodium, potassium, ammonium or triethanolammonium.

Non-limiting examples of aspartate surfactants are sodium lauroyl aspartate, sodium myristoyl aspartate, sodium cocoyl aspartate, sodium caproyl aspartate, di-sodium lauroyl aspartate, di-sodium myristoyl aspartate, di-sodium cocoyl aspartate, di-sodium caproyl aspartate, potassium lauroyl aspartate, potassium myristoyl aspartate, potassium cocoyl aspartate, potassium caproyl aspartate, di-potassium lauroyl aspartate, di-potassium myristoyl aspartate, di-potassium cocoyl aspartate, di-potassium caproyl aspartate, and mixtures thereof.

Cationic surfactants present may act as conditioning agents and assist in the heating step by ensuring that the heating device runs smoothly over the hair fibers. While the surfactants may also help to increase viscosity, they are not considered as rheology modifiers for purposes of describing the exemplary embodiment herein.

The cationic surfactants can be any of the cationic surfactants known or previously used in the art of aqueous surfactant compositions. Suitable classes of cationic surfactants alkyl amines, alkyl imidazolines, ethoxylated amines, quaternary compounds, and quaternized esters. In addition, alkyl amine oxides can function as a cationic surfactant at a low pH.

Alkyl amine surfactants can be salts of primary, secondary and tertiary fatty $C_{12}$-$C_{22}$ alkylamines, substituted or unsubstituted, and substances sometimes referred to as "amidoamines". Examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Examples of amidoamines and salts thereof include stearamido propyl dimethyl amine, stearamidopropyl dimethylamine citrate, palmitamidopropyl diethylamine, and cocamidopropyl dimethylamine lactate.

Examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Examples of ethyoxylated amines include PEG-cocopolyamine, PEG-15 tallow amine, quaternium-52, and the like.

Among the quaternary ammonium compounds useful as cationic surfactants, some correspond to the general formula: $(R^5R^6R^7R^8N^+)$ $E^-$, wherein $R^5$, $R^6$, $R^7$, and $R^8$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g., chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher ($C_{10}$-$C_{32}$ in the alkyl chain), can be saturated or unsaturated. In one aspect, the aryl groups are selected from phenyl and benzyl.

Exemplary quaternary ammonium surfactants include, but are not limited to cetyl trimethylammonium chloride (cetrimonium chloride), cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride (behentrimonium chloride), benzalkonium chloride, benzethonium chloride, and di(coconutalkyl) dimethyl ammonium chloride, ditallowdimethyl ammonium chloride, di(hydrogenated tallow) dimethyl ammonium chloride, di(hydrogenated tallow) dimethyl ammonium acetate, ditallowdimethyl ammonium methyl sulfate, ditallow dipropyl ammonium phosphate, and ditallow dimethyl ammonium nitrate.

At low pH, amine oxides can protonate and behave similarly to N-alkyl amines. Examples include, but are not limited to, dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

At low pH, amine oxides can protonate and behave similarly to N-alkyl amines. Examples include, but are not limited to, dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

In one aspect of the present technology, suitable amphoteric surfactants include but are not limited to alkyl betaines, e.g., lauryl betaine; alkylamido betaines, e.g., cocamidopropyl betaine and cocohexadecyl dimethylbetaine; alkylamido sultaines, e.g., cocamidopropyl hydroxysultaine; (mono- and di-) amphocarboxylates, e.g., sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate; and mixtures thereof.

The foregoing amphoteric surfactants (i.e., the betaines and sultaines are disclosed without a counter ion, as one of ordinary skill in the art will recognize that the under the pH conditions of the compositions containing the amphoteric surfactants, these surfactants are either electrically neutral by virtue of having balancing positive and negative charges, or they contain counter ions such as alkali metal, alkaline earth or ammonium ions as a charge balancing moiety.

The nonionic surfactant can be any of the nonionic surfactants known or previously used in the art of aqueous surfactant compositions. Suitable nonionic surfactants include, but are not limited to, aliphatic ($C_6$-$C_{18}$) primary or secondary linear or branched chain acids, alcohols or phenols; alkyl ethoxylates; alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers. Other suitable nonionic surfactants include mono- or dialkyl alkanolamides; alkyl polyglucosides (APGs); sorbitan fatty acid esters; polyoxyethylene sorbitan fatty acid esters; polyoxyethylene sorbitol esters; polyoxyethylene acids, and polyoxyethylene alcohols. Other examples of suitable nonionic surfactants include coco mono- or diethanolamide, coco glucoside, decyl diglucoside, lauryl diglucoside, coco diglucoside, polysorbate 20, 40, 60, and 80, ethoxylated linear alcohols, cetearyl alcohol, lanolin alcohol, stearic acid, glyceryl stearate, PEG-100 stearate, laureth 7, and oleth 20.

In another embodiment, non-ionic surfactants include alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, Glucamate™ VLT and Glucamate™ SSE-20, respectively, are also suitable. Other exemplary hydrophobically modified alkoxylated methyl glucosides are disclosed in U.S. Pat. Nos. 6,573,375 and 6,727,357.

Other surfactants which can be utilized in the composition are set forth in more detail in WO 99/21530, U.S. Pat. Nos. 3,929,678, 4,565,647, 5,720,964, and 5,858,948. In addition, suitable surfactants are also described in *McCutcheon's Emulsifiers and Detergents* (North American and International Editions, by Schwartz, Perry and Berch).

While the amounts of the surfactant utilized in a composition comprising the exemplary thermally-activated agent can vary widely depending on a desired application, the amounts which are often utilized generally range from 1 wt. % to 80 wt. %, on an actives basis. For example, the surfactant may be present in the composition, on an actives basis, at a total concentration of 0.001-20 wt. %, e.g., at least 0.1 wt. %.

Conditioning Agents

Cationic Polymers

Cationic polymers are components that can enhance the delivery of conditioning agents and/or provide auxiliary conditioning benefits to the hair, scalp or skin to improve and enhance the conditioning benefits delivered by the silicone conditioning agents of the disclosed technology. Cationic polymer refers to polymers containing at least one cationic moiety or at least one moiety that can be ionized to form a cationic moiety. Typically, these cationic moieties are nitrogen containing groups such as quaternary ammonium or protonated amino groups. The cationic protonated amines can be primary, secondary, or tertiary amines. The cationic polymer typically has a cationic charge density ranging from about 0.2 to about 7 meq/g at the pH of the intended use of the composition. The average molecular weight of the cationic polymer ranges from about 5,000 daltons to about 10,000,000 daltons.

Non-limiting examples of such polymers are described in the CTFA *International Cosmetic Ingredient Dictionary/ Handbook* via the CTFA website as well as the CTFA *Cosmetic Ingredient Handbook*, Ninth Ed., Cosmetic and Fragrance Assn., Inc., Washington D.C. (2002), incorporated herein by reference, can be used.

Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (CTFA, Polyquaternium-16); copolymers of 1-vinyl-2-pyrrolidone and dimethylaminoethyl methacrylate (CTFA, Polyquaternium-11); cationic diallyl quaternary ammonium-containing polymers, including, for example, dimethyldiallylammonium chloride homopolymer, copolymers of acrylamide and dimethyldiallylammonium chloride (CTFA, Polyquaternium-6 and Polyquaternium-7, respectively); amphoteric copolymers of acrylic acid including copolymers of acrylic acid and dimethyldiallylammonium chloride (CTFA, Polyquaternium-22); terpolymers of acrylic acid with dimethyldiallylammonium chloride and acrylamide (CTFA, Polyquaternium-39); terpolymers of acrylic acid with methacrylamidopropyl trimethylammonium chloride and methylacrylate (CTFA, Polyquaternium-47); terpolymers of acrylic acid, methacrylamidopropyl trimethylammonium chloride and acrylamide (CTFA, Polyquaternium-53). In one aspect suitable cationic substituted monomers are the cationic substituted dialkylaminoalkyl acrylamides, dialkylaminoalkyl methacrylamides, and combinations thereof.

Other suitable cationic polymers for use in the composition include polysaccharide polymers, such as cationic cellulose derivatives and cationic starch derivatives modified with a quaternary ammonium halide moiety. Exemplary cationic cellulose polymers are salts of hydroxyethyl cellulose reacted with trimethyl ammonium substituted epoxide (CTFA, Polyquaternium-10). Other suitable types of cationic cellulose include the polymeric quaternary ammonium salts of hydroxyethyl cellulose reacted with lauryl dimethyl ammonium substituted epoxide (CTFA, Polyquaternium-24).

Other suitable cationic polymers include cationic polygalactomannan derivatives such as guar gum derivatives and cassia gum derivatives, e.g., guar hydroxypropyltrimonium chloride and cassia hydroxypropyltrimonium chloride, respectively. Guar hydroxypropyltrimonium chloride is commercially available under the Jaguar™ trade name series from Rhodia Inc. and the N-Hance trade name series from Ashland Inc. Cassia hydroxypropyltrimonium chloride is commercially available under the Sensomer™ trade name series from Lubrizol Advanced Materials, Inc.

The amount of cationic polymer that may be utilized in the cleansing compositions of the disclosed technology range from about 0.01 to about 10 wt. % in one aspect, from about 0.05 to about 3 wt. % in another aspect, and from about 0.1 to about 1 wt. % in a further aspect, based on the weight of the total composition.

Silicones

Silicone hair conditioning agent phase can be used in the composition, such as a silicone fluid and can also comprise other ingredients, such as a silicone resin, to improve silicone fluid deposition efficiency or enhance the glossiness of the hair especially when high refractive index (e.g. above about 1.46). The optional silicone hair conditioning agent phase may comprise volatile silicone, nonvolatile silicone, or combinations thereof. The silicone droplets are typically suspended with an optional suspending agent. The silicone conditioning agent particles may comprise volatile silicone, non-volatile silicone, or combinations thereof. Preferred are non-volatile silicone conditioning agents. If volatile silicones are present, they will typically be incidental to their use as a solvent or carrier for commercially available forms of non-volatile silicone materials ingredients, such as silicone gums and resins. The silicone hair conditioning agents for use in the disclosed technology have a viscosity of from about 20 to about 2,000,000 centistokes (1 centistokes equals $1\times10^{-6}$ m$^2$/s) in one aspect, from about 1,000 to about 1,800,000 centistokes in another aspect, from about 50,000 to about 1,500,000 in a further aspect, and from about 100,000 to about 1,500,000 centistokes in a still further aspect, as measured at 25° C.

The concentration of the silicone conditioning agent can range from about 0.01% to about 10%, by weight of the composition in which it is included. In another aspect the amount of silicone conditioning agent ranges from about 0.1% to about 8%, from about 0.1% to about 5% in still another aspect, and from about 0.2% to about 3% by wt. in a further aspect, all based on the total weight of the composition.

In one embodiment, the dispersed silicone conditioning agent particles can have a volume average particle diameter ranging from about 5 μm to about 125 μm. For small particle application to hair, the volume average particle diameters range from about 0.01 μm to about 4 μm in one aspect, from about 0.01 μm to about 2 μm in another aspect, and from about 0.01 μm to about 0.5 μm in still another aspect. For larger particle application to hair, the volume average particle diameters typically range from about 5 μm to about 125 μm in one aspect, from about 10 μm to about 90 μm in another aspect, from about 15 μm to about 70 μm in still another aspect, and from about 20 μm to about 50 μm in a further aspect.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989), incorporated herein by reference. Silicone fluids are generally described as alkylsiloxane polymers. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

Silicone fluids include silicone oils, which are flowable silicone materials having a viscosity, as measured at 25° C. of less than 1,000,000 csk, and typically range from about about 5 csk to about 1,000,000 csk. Suitable silicone oils include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl, polyaryl siloxanes, or polyalkylaryl siloxanes which conform to the following formula:

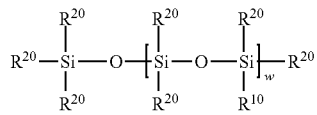

wherein $R^{20}$ is aliphatic, independently selected from alkyl, alkenyl, and aryl, $R^{20}$ can be substituted or unsubstituted, and w is an integer from 1 to about 8,000. Suitable unsubstituted $R^{20}$ groups for use in the personal cleansing compositions of the disclosed technology include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable $R^{20}$ groups also include cationic amines and quaternary ammonium groups.

In one aspect of the disclosed technology, exemplary $R^{20}$ alkyl and alkenyl substituents range from $C_1$-$C_5$ alkyl and alkenyl, from $C_1$-$C_4$ in another aspect, from $C_1$-$C_2$ in a further aspect. The aliphatic portions of other alkyl-, alkenyl-, or alkynyl-containing groups (such as alkoxy, alkaryl, and alkamino) can be straight or branched chains, and range from $C_1$-$C_5$ in one aspect, from $C_1$-$C_4$ in another aspect, and from $C_1$-$C_2$ in a further aspect. As discussed above, the $R^{20}$ substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is as described above.

Exemplary siloxanes are polydimethyl siloxane, polydiethylsiloxane, and polymethylphenylsiloxane. These siloxanes are available, for example, from the General Electric Company in their Viscasil R and SF 96 series, and from Dow Corning marketed under the Dow Corning 200 series. Exemplary polyalkylaryl siloxane fluids that may be used, include, for example, polymethylphenylsiloxanes. These siloxanes are available, for example, from the General Electric Company as SF 1075 methyl phenyl fluid or from Dow Corning as 556 Cosmetic Grade Fluid.

Cationic silicone fluids are also suitable for use in the disclosed technology. The cationic silicone fluids can be represented, but are not limited, to the general formula):

$(R^{21})_eG_{3-f}$—Si—$(OSiG_2)_g$—$(OSiG_f(R_1)_{(2-f)h}$—O— $SiG_{3-e}(R^{21})_f$ wherein G is hydrogen, phenyl, hydroxy, or $C_1$-$C_8$ alkyl, preferably methyl; e is 0 or an integer having of from 1 to 3; f is 0 or 1; g is a number from 0 to 1,999; h is an integer from 1 to 2,000, preferably from 1 to 10; the sum of g and h is a number from 1 to 2,000 in one aspect, and from 50 to 500 in another aspect of the disclosed technology; $R^{21}$ is a monovalent radical conforming to the general formula $C_qH_{2q}L$, wherein q is an integer having a value from 2 to 8 and L is selected from the following groups:

—N($R^{22}$)CH$_2$CH$_2$N($R^{22}$)$_2$     a)

—N($R^{22}$)     b)

—N($R^{22}$)$_3$CA$^-$     c)

—N($R^{22}$)CH$_2$CH$_2$N($R^{22}$)$_2$H$_2$CA$^-$     d)

wherein $R^{22}$ is independently selected from hydrogen, $C_1$-$C_{20}$ alkyl, phenyl, benzyl; and A$^-$ is a halide ion selected from chloride, bromide, fluoride, and iodide.

An exemplary cationic silicone corresponding to the previous formula defined immediately above is the polymer known as "trimethylsilylamodimethicone" of formula:

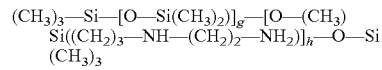

Another cationic silicone useful in the disclosed technology can be represented by the formula:

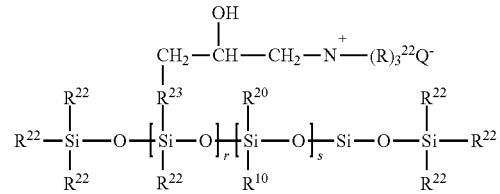

wherein where $R^{22}$ represents a radical selected from a $C_1$-$C_{18}$ alkyl and $C_1$-$C_{18}$ alkenyl radical; $R^{23}$ independently represents a radical selected from a $C_1$-$C_{18}$ alkylene radical or a $C_1$-$C_{18}$ alkyleneoxy radical; Q is a halide ion; r denotes an average statistical value from 2 to 20 in one aspect, and from 2 to 8 in another aspect; s denotes an average statistical value from 20 to 200 in one aspect, and from 20 to 50 in another aspect. In one aspect $R^{22}$ is methyl. In another aspect Q is chloride.

Other optional silicone fluids are the insoluble silicone gums. These gums are polysiloxane materials having a viscosity at 25° C. of greater than or equal to 1,000,000 centistokes. Silicone gums are described in U.S. Pat. No. 4,152,416; Noll and Walter, Chemistry and Technology of Silicones, N.Y.: Academic Press 1968; and in General Electric Silicone Rubber Product Data Sheets SE 30, SE 33, SE 54 and SE 76, all of which are incorporated herein by reference. The silicone gums will typically have a mass molecule weight in excess of about 200,000 Daltons, generally between about 200,000 to about 1,000,000 Daltons, specific examples of which include polydimethylsiloxane, polydimethylsiloxane/methylvinylsiloxane copolymer, polydimethylsiloxane/diphenyl siloxane/methylvinylsiloxane) copolymer, and mixtures thereof.

Another category of nonvolatile, insoluble silicone fluid conditioning agents are the high refractive index polysiloxanes, having a refractive index of at least about 1.46 in one aspect, at least about 1.48 in another aspect, at least about 1.52 in a further aspect, and at least about 1.55 in a still further aspect. The refractive index of the polysiloxane fluid will generally be less than about 1.70, typically less than about 1.60. In this context, polysiloxane "fluid" includes oils as well as gums.

The high refractive index polysiloxane fluid includes those represented by the general formula set forth for the polyalkyl, polyaryl, and polyalkylaryl siloxanes described above, as well as cyclic polysiloxanes (cyclomethicones) represented by the formula:

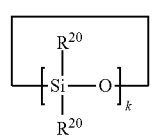

wherein the substituent $R^{20}$ is as defined above, and the number of repeat units, k, ranges from about 3 to about 7 in one aspect, and from 3 to 5 in another aspect. The high refractive index polysiloxane fluids can contain an amount of aryl containing $R^{20}$ substituents sufficient to increase the refractive index to the desired level, which is described above. Additionally, $R^{20}$ and k must be selected so that the material is non-volatile. Aryl containing substituents include those which contain alicyclic and heterocyclic five and six member aryl rings and those which contain fused five or six member rings. The aryl rings can be substituted or unsubstituted. Substituents include aliphatic substituents, and can also include alkoxy substituents, acyl substituents, ketones, halogens (e.g., Cl and Br), amines, etc. Exemplary aryl containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g. phenyl $C_2$-$C_4$ alkynes). Heterocyclic aryl groups include substituents derived from furan, imidazole, pyrrole, pyridine, etc. Fused aryl ring substituents include, for example, naphthalene, coumarin, and purine.

The high refractive index polysiloxane fluids will have a degree of aryl containing substituents of at least about 15% by wt. in one aspect, at least about 20% by wt. in another aspect, at least about 25% by wt. in a further aspect, at least about 35% by wt. in still further aspect, and at least about 50% by wt. in an additional aspect, based on the wt. of the polysiloxane fluid. Typically, the degree of aryl substitution will be less than about 90% by wt., more typically less than about 85% by wt., and can generally ranges from about 55% to about 80% by wt. of the polysiloxane fluid.

In another aspect, the high refractive index polysiloxane fluids have a combination of phenyl or substituted phenyl derivatives. The substituents can be selected from $C_1$-$C_4$ alkyl (e.g., methyl), hydroxy, and $C_1$-$C_4$ alkylamino (e.g., —$R^{24}NHR^{25}NH_2$ wherein each $R^{24}$ and $R^{25}$ group independently is a $C_1$-$C_3$ alkyl, alkenyl, and/or alkoxy).

When high refractive index silicones are used in the compositions of the present technology, they optionally can be used in solution with a spreading agent, such as a silicone resin or a surfactant, to reduce the surface tension by a sufficient amount to enhance spreading and thereby enhance the glossiness (subsequent to drying) of hair treated with such compositions. Silicone fluids suitable for use in the compositions of the present technology are disclosed in U.S. Pat. Nos. 2,826,551, 3,964,500, 4,364,837, British Pat. No. 849,433, and Silicon Compounds, Petrarch Systems, Inc. (1984), all of which are incorporated herein by reference. High refractive index polysiloxanes are available from Dow Corning Corporation (Midland, Mich.) Huls America (Piscataway, N.J.), and General Electric Silicones (Waterford, N.Y.).

Silicone resins can be included in the silicone conditioning agent suitable for use in the present composition. These resins are crosslinked polysiloxanes. The crosslinking is introduced through the incorporation of trifunctional and tetrafunctional silanes with monofunctional or difunctional (or both) silanes during manufacture of the silicone resin.

As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. In one aspect, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and terachlorosilane, with the methyl-substituted silanes being most commonly utilized. Silicone resins are offered by General Electric as GE SS4230 and SS4267.

Silicone materials and silicone resins in particular, are identified according to a shorthand nomenclature system known to those of ordinary skill in the art as "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence. Typical alternate substituents include groups such as vinyl, phenyls, amines, hydroxyls, etc. The molar ratios of the various units, either in terms of subscripts to the symbol indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

Exemplary silicone resins for use in the compositions of the present technology include, but are not limited to MQ, MT, MTQ, MDT and MDTQ resins. In one aspect, methyl is the silicone resin substituent. In another aspect, the silicone resin is selected from a MQ resins, wherein the M:Q ratio is from about 0.5:1.0 to about 1.5:1.0 and the average molecular weight of the silicone resin is from about 1000 to about 10,000 Daltons.

When employed with non-volatile silicone fluids having a refractive index below 1.46, the weight ratio of the non-volatile silicone fluid to the silicone resin component, ranges from about 4:1 to about 400:1 in one aspect, from about 9:1 to about 200:1 in another aspect, from about 19:1 to about 100:1 in a further aspect, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e., the conditioning active, the sum of the fluid and resin should be included in determining the level of silicone conditioning agent in the composition.

The volatile silicones described above include cyclic and linear polydimethylsiloxanes, and the like. Cyclic volatile silicones (cyclomethicones) typically contain about 3 to about 7 silicon atoms, alternating with oxygen atoms, in a cyclic ring structure such as described above for the non-volatile cyclic silicones. However, each $R^{20}$ substituent and repeating unit, k, in the formula must be selected so that the material is non-volatile. Typically $R^{20}$ is substituted with two alkyl groups (e.g., methyl groups). The linear volatile silicones are silicone fluids, as described above, having viscosities of not more than about 25 mPas. "Volatile"

means that the silicone has a measurable vapor pressure, or a vapor pressure of at least 2 mm of Hg at 20° C. Non-volatile silicones have a vapor pressure of less than 2 mm Hg at 20° C. A description of cyclic and linear volatile silicones is found in Todd and Byers, "Volatile Silicone Fluids for Cosmetics", Cosmetics and Toiletries, Vol. 91(1), pp. 27-32 (1976), and in Kasprzak, "Volatile Silicones", Soap/Cosmetics/Chemical Specialities, pp. 40-43 (December 1986), each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning® 244, 245, 246, 345, and 1401 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200° Fluid (e.g., product designations 0.65 CST, 1 CST, 1.5 CST, and 2 CST) and Dow Corning® 2-1184 Fluid.

Emulsified silicones are also suitable for combination in the disclosed technology. Typically silicone emulsions have an average silicone particle size in the composition of less than 30 μm in one aspect, less than 20 μm in another aspect, and less than 10 μm in a further aspect. In one embodiment of the disclosed technology, the average silicone particle size of the emulsified silicone in the composition is less than 2 μm, and ideally it ranges from 0.01 to 1 μm. Silicone emulsions having an average silicone particle size of <0.15 micrometers are generally termed micro-emulsions. Particle size may be measured by means of a laser light scattering technique, using a 2600D Particle Sizer from Malvern Instruments. Suitable silicone emulsions for use in the disclosed technology are also commercially available in a pre-emulsified form. Examples of suitable pre-formed emulsions include emulsions DC2-1766, DC2-1784, and micro-emulsions DC2-1865 and DC2-1870, all available from Dow Corning. These are all emulsions/micro-emulsions of dimethiconol. Crosslinked silicone gums are also available in a pre-emulsified form, which is advantageous for ease of formulation. An exemplary material is available from Dow Corning as DC X2-1787, which is an emulsion of crosslinked dimethiconol gum. Another exemplary material is available from Dow Corning as DC X2-1391, which is a micro-emulsion of crosslinked dimethiconol gum. Preformed emulsions of amino functional silicone are also available from suppliers of silicone oils such as Dow Corning and General Electric. Particularly suitable are emulsions of amino functional silicone oils with non ionic and/or cationic surfactant. Specific examples include DC929 Cationic Emulsion, DC939 Cationic Emulsion, DC949 Cationic emulsion, and the non-ionic emulsions DC2-7224, DC2-8467, DC2-8177 and DC2-8154 (all available from Dow Corning). Mixtures of any of the above types of silicone may also be used. Specific examples of amino functional silicones suitable are the aminosilicone oils DC2-8220, DC2-8166, DC2-8466, and DC2-8950-114 (all available from Dow Corning), and GE 1149-75, (ex General Electric Silicones). An example of a quaternary silicone polymer useful in the disclosed technology is the material K3474, available from Goldschmidt, Germany.

Other suitable silicone oils include the dimethicone copolyols, which are linear or branched copolymers of dimethylsiloxane (dimethicone) modified with alkylene oxide units. The alkylene oxide units can be arranged as random or block copolymers. A generally useful class of dimethicone polyols are block copolymers having terminal and/or pendent blocks of polydimethylsiloxane and blocks of polyalkylene oxide, such as blocks of polyethylene oxide, polypropylene oxide, or both. Dimethicone copolyols can be water soluble or insoluble depending on the amount of polyalkylene oxide present in the dimethicone polymer and can be anionic, cationic, or nonionic in character.

The water soluble or water dispersible silicones can also be used in the disclosed technology. Such water soluble silicones contain suitable anionic functionality, cationic functionality, and/or nonionic functionality to render the silicone water soluble or water dispersible. In one embodiment, the water soluble silicones contain a polysiloxane main chain to which is grafted at least one anionic moiety. The anionic moiety can be grafted to a terminal end of the polysiloxane backbone, or be grafted as a pendant side group, or both. By anionic group is meant any hydrocarbon moiety that contains at least one anionic group or at least one group that can be ionized to an anionic group following neutralization by a base. As discussed previously, the quantity of the hydrocarbon groups of anionic character which are grafted onto the silicone chain are chosen so that the corresponding silicone derivative is water-soluble or water-dispersible after neutralization of the ionizable groups with a base. The anionic silicone derivatives can be selected from existing commercial products or can be synthesized by any means known in the art. The nonionic silicones contain alkylene oxide terminal and/or pendant side chain units (e.g., dimethicone copolyols).

Silicones with anionic groups can be synthesized by reaction between (i) a polysiloxane containing a silinic hydrogen and (ii) a compound containing olefinic unsaturation that also contains an anionic functional group. Exemplary of such a reaction is the hydrosilylation reaction between poly(dimethylsiloxanes) containing a Si—H group(s) and an olefin, $CH_2$=.$CHR^{26}$, wherein $R^{26}$ represents a moiety containing an anionic group. The olefin can be monomeric, oligomeric or polymeric. Polysiloxane compounds that contain a pendant reactive thio (—SH) group(s) are also suitable for grafting an unsaturated anionic group containing compound to the poly(siloxane) backbone.

According to one aspect of the disclosed technology, the anionic monomers containing ethylenic unsaturation are used alone or in combination and are selected from linear or branched, unsaturated carboxylic acids. Exemplary unsaturated carboxylic acids are acrylic acid, methacrylic acid, maleic acid, maleic anhydride, itaconic acid, fumaric acid and crotonic acid. The monomers can optionally be partially or completely neutralized by base to form an alkali, alkaline earth metal, and ammonium salt. Suitable bases include but are not limited to the alkali, alkaline earth (e.g., sodium, potassium, lithium, calcium) and ammonium hydroxides. It will be noted that, similarly, the oligomeric and polymeric graft segments formed from the forgoing monomers can be post-neutralized with a base (sodium hydroxide, aqueous ammonia, etc) to form a salt. Examples of silicone derivatives which are suitable for use in the disclosed technology are described in patent applications numbers EP-A-0 582, 152 and WO 93/23009. An exemplary class of silicone polymers are the polysiloxanes containing repeat units represented by the following structure:

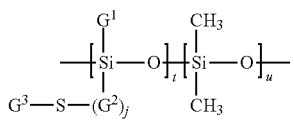

wherein $G^1$ represents hydrogen, $C_1$-$C_{10}$ alkyl and phenyl radical; $G^2$ represents alkylene; $G^3$ represents an anionic polymeric residue obtained from the polymerization of at least one anionic monomer containing ethylenic unsaturation; j is 0 or 1; t is an integer ranging from 1 to 50; and u is an integer from 10 to 350. In one embodiment of the disclosed technology, $G^1$ is methyl; j is 1; and G2 is propylene radical; $G^3$ represents a polymeric radical obtained from the polymerization of at least one unsaturated monomer containing a carboxylic acid group (e.g., acrylic acid, methacrylic acid, itaconic acid, fumaric acid, crotonic acid, maleic acid, or aconitic acid, and the like).

The carboxylate group content in the final polymer preferably ranges from 1 mole of carboxylate per 200 g of polymer to 1 mole of carboxylate per 5000 g of polymer. The number molecular mass of the silicone polymer preferably ranges from 10,000 to 1,000,000 and still more preferably from 10,000 to 100,000. Exemplary unsaturated monomers containing carboxylic acid groups are acrylic acid and methacrylic acid. In addition, to the carboxylic acid group containing monomers, $C_1$-$C_{20}$ alkyl esters of acrylic acid and methacrylic acid can be copolymerized into the polymeric backbone. Exemplary esters include but are not limited to the ethyl and butyl esters of acrylic and methacrylic acid. A commercially available silicone-acrylate polymer is marketed by the 3M Company under the trademark Silicones "Plus" Polymer 9857C (VS80 Dry). These polymers contain a polydimethylsiloxanes (PDMS) backbone onto which is grafted (through a thiopropylene group) random repeating units of poly(meth)acrylic acid and the butyl ester of poly(meth)acrylate. These products can be obtained conventionally by radical copolymerization between thiopropyl functionalized polydimethylsiloxane and a mixture of monomers comprising (meth)acrylic acid and of butyl(meth) acrylate.

In another embodiment the water soluble silicone copolyol useful in the practice of the disclosed technology can be represented silicone copolyol carboxylates represented by the formula:

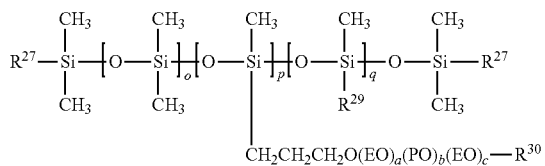

where $R^{27}$ and $R^{28}$ are independently selected from $C_1$-$C_{30}$ alkyl, $C_6$-$C_{14}$ aryl, $C_7$-$C_{15}$ aralkyl, $C_1$-$C_{15}$ alkaryl, or an alkenyl group of 1 to 40 carbons, hydroxyl, —R31-G' or —$(CH_2)_3O(EO)_a(PO)_b(EO)_c$-G', with the proviso that both $R^{27}$ and $R^{28}$ are not methyl; $R^{29}$ is selected from $C_1$-$C_5$ alkyl or phenyl; in this formula a, b, and c are integers independently ranging from 0 to 100; EO is ethylene oxide, —($CH_2CH_2O$)—; PO is propylene oxide, —($CH_2CH(CH_3)$ O)—; in this formula o is an integer ranging from 1 to 200, p is an integer ranging from 0 to 200, and q is an integer ranging from 0 to 1000; $R^{39}$ is hydrogen, $C_1$-$C_{30}$ alkyl, aryl, $C_7$-$C_{15}$ aralkyl, $C_7$-$C_{15}$ alkaryl, or alkenyl group of 1 to 40 carbons or —C(O)—X wherein X is $C_1$-$C_{30}$ alkyl, $C_6$-$C_{14}$ aryl, $C_7$-$C_{15}$ aralkyl, $C_1$-$C_{15}$alkaryl, or an alkenyl group of 1 to 40 carbons, or a mixture thereof; $R^{31}$ is a divalent group selected from alkylene radical of 1 to 40 carbon atoms which may be interrupted with arylene group of 6 to 18 carbons or an alkylene group containing unsaturation of 2 to 8 carbons; and G' is independently are selected from:

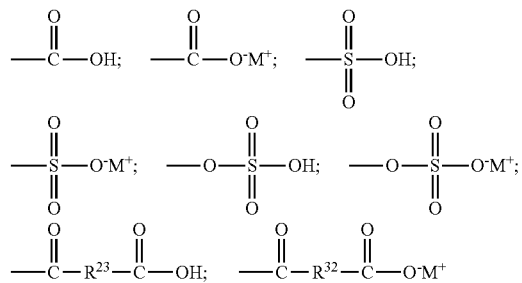

where $R^{32}$ is a divalent group selected from alkylene of 1 to 40 carbons, an unsaturated group containing 2 to 5 carbon atoms, or an arylene group of 6 to 12 carbon atoms; where M is a cation selected from Na, K, Li, $NH_4$, or an amine containing $C_1$-$C_{10}$ alkyl, $C_6$-$C_{14}$ aryl (e.g., phenyl, naphthyl), $C_2$-$C_{10}$ alkenyl, hydroxyalkyl, $C_7$-$C_{24}$ arylalkyl or $C_7$-$C_{24}$ alkaryl groups. Representative $R^{32}$ radicals are: —$CH_2CH_2$—, —CH=CH—, —CH=$CHCH_2$—, and phenylene.

In another embodiment the water-soluble silicones useful in the practice of the disclosed technology can be represented an anionic silicone copolyol represented by the formula:

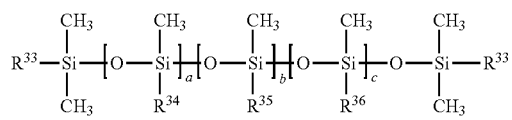

where is $R^{33}$ is methyl or hydroxyl; $R^{34}$ is selected from $C_1$-$C_8$ alkyl or phenyl; $R^{35}$ represents the radical —$(CH_2)_3O(EO)_x(PO)_y(EO)_z$—$SO_3^-M^+$; where M is a cation selected from Na, K, Li, or $NH_4$; in this formula x, y and z are integers independently ranging from 0 to 100; $R^{36}$ represents the radical —$(CH_2)_3O(EO)_x(PO)_y(EO)_z$—H; in this formula a and c are independently integers ranging from 0 to 50, and b is an integer ranging from 1 to 50; EO is ethylene oxide, e.g., —($CH_2CH_2O$)—; PO is propylene oxide, e.g., —($CH_2CH(CH_3)O$)—.

In still another embodiment the water-soluble silicones useful in the practice of the disclosed technology can be represented an anionic silicone copolyol represented by the formula:

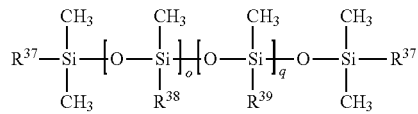

wherein $R^{37}$ and $R^{38}$ independently are —$CH_3$ or a radical represented by: —$(CH_2)_3O(EO)_a(PO)_b(EO)_c$—C(O)—$R^{40}$—C(O)OH, subject to the proviso that both $R^{37}$ and $R^{38}$ are not —$CH_3$ at the same time; $R^{40}$ is selected from the divalent radical —$CH_2CH_2$, —CH=CH—, and phenylene; $R^{39}$ is selected from $C_1$-$C_5$ alkyl or phenyl; in this formula a, b and c are integers independently ranging from 0 to 20; EO is an ethylene oxide residue, e.g., —$(CH_2CH_2O)$—; PO is a propylene oxide residue, e.g., —$(CH_2CH(CH_3)O)$—; in this formula o is an integer ranging from 1 to 200 and q is an integer ranging from 0 to 500.

Other water-soluble silicones useful in the disclosed technology are quaternized silicone copolyol polymers. These polymers have a pendant quaternary nitrogen functional group present and are represented by the formula:

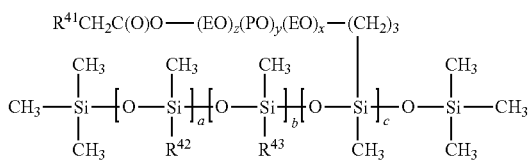

where $R^{41}$ represents a quaternary substituent—$N^+R^3R^4R^5$ $X^-$, wherein $R^3$ and $R^4$, and $R^5$, independently, are selected from hydrogen and linear and branched $C_1$-$C_{24}$ alkyl, and $X^-$ represents an anion suitable to balance the cationic charge on the nitrogen atom; $R^{42}$ is selected from $C_1$-$C_{10}$ alkyl and phenyl; $R^{43}$ is —$(CH_2)_3O(EO)_x(PO)_y(EO)_z$—H, where EO is an ethylene oxide residue, e.g., —$(CH_2CH_2O)$—; PO is a propylene oxide residue, e.g., —$(CH_2CH(CH_3)O)$—; in this formula a is an integer from 0 to 200, b is an integer from 0 to 200, and c is an integer from 1 to 200; in this formula x, y and z are integers and are independently selected from 0 to 20. In one aspect, the anion $X^-$ represents an anion selected from chloride, bromide, iodide, sulfate, methylsulfate, sulfonate, nitrate, phosphate, and acetate.

Other suitable water-soluble silicones are amine substituted silicone copolyols represented by the formula:

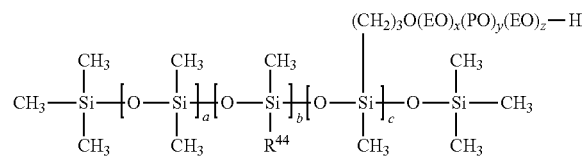

where $R^{44}$ is selected from —$NH(CH_2)_nNH_2$ or —$(CH_2)_nNH_2$, where in this formula n is an integer from 2 to 6; and x, is n integer from 0 to 20; where EO is an ethylene oxide residue, e.g., —$(CH_2CH_2O)$—; PO is a propylene oxide residue, e.g., —$(CH_2CH(CH_3)O)$—; in this formula a is an integer from 0 to 200, b is an integer from 0 to 200, and c is an integer from 1 to 200; in this formula x, y and z are integers and are independently selected from 0 to 20.

Still other water-soluble silicones can be selected from nonionic silicone copolyols (dimethicone copolyols) represented by the formula:

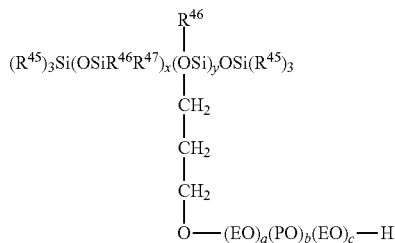

where $R^{45}$, independently, represents a radical selected from $C_1$-$C_{30}$ alkyl, $C_6$-$C_{14}$ aryl, and $C_2$-$C_{20}$ alkenyl; $R^{46}$ represents a radical selected from $C_1$-$C_{30}$ alkyl, $C_6$-$C_{14}$ aryl, and $C_2$-$C_{20}$ alkenyl; EO is an ethylene oxide residue, e.g., —$(CH_2CH_2O)$—; PO is a propylene oxide residue, e.g., —$(CH_2CH(CH_3)O)$—; in this formula a, b, and c are, independently, 0 to 100; in this formula x is 0 to 200; and y is 1 to 200.

In another embodiment water soluble silicones can be selected from nonionic silicone copolyols represented by the formula:

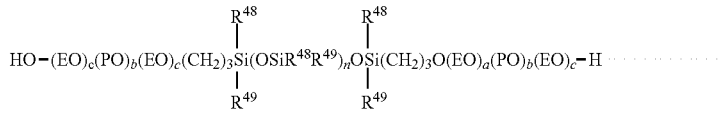

wherein $R^{48}$ and $R^{49}$, independently, represent a radical selected from $C_1$-$C_{30}$ alkyl, $C_6$-$C_{14}$ aryl, and $C_2$-$C_{20}$ alkenyl; EO is an ethylene oxide residue, e.g., —$(CH_2CH_2O)$—; PO is a propylene oxide residue, e.g., —$(CH_2CH(CH_3)O)$—; in this formula a, b, and c are independently 0 to 100; and in this formula n is 0 to 200.

In the copolyol embodiments set forth above, the EO and PO residues can be arranged in random, non-random, or blocky sequences.

Dimethicone copolyols are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi); Dow Corning® 5103 and 5329 from Dow Corning Corporation; and Abil® dimethicone copolyols, such as, for example WE 09, WS 08, EM 90 and EM 97 from Evonik Goldschmidt Corporation; and Silsense™ dimethicone copolyols, such as Silsense Copolyol-1 and Silsense Copolyol-7, available from Lubrizol Advanced Materials, Inc.

The silicone can be added from about 0.05% to about 20%, by weight of the composition in one aspect, from about 0.08% to about 5% in another aspect, and from about 0.1% to about 3% in a further aspect either alone or in combination with other conditioning agents, described below.

Suitable conditioning oils for use as conditioning agents in the compositions of the disclosed technology include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils typically contain about 12 to 19 carbon atoms. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from BP Chemical Company.

Natural oil conditioners are also useful in the practice of disclosed technology and include but are not limited to peanut, sesame, avocado, coconut, cocoa butter, almond, safflower, corn, cotton seed, sesame seed, walnut oil, castor, olive, jojoba, palm, palm kernel, soybean, wheat germ, linseed, sunflower seed; eucalyptus, lavender, vetiver, litsea, cubeba, lemon, sandalwood, rosemary, chamomile, savory, nutmeg, cinnamon, hyssop, caraway, orange, geranium, cade, and bergamot oils, fish oils, glycerol tricaprocaprylate; and mixtures thereof. The natural oils can also be utilized as emollients.

Natural and synthetic wax conditioning agents can be employed in the compositions of the disclosed technology, including but are not limited to carnauba wax, candelila wax, alfa wax, paraffin wax, ozokerite wax, olive wax, rice wax, hydrogenated jojoba wax, bees wax, modified bees wax, e.g., cerabellina wax, marine waxes, polyolefin waxes, e.g., polyethylene wax; and mixtures thereof.

Liquid polyolefin conditioning oils can be used in the compositions of the disclosed technology. The liquid polyolefin conditioning agents are typically poly-α-olefins that have been hydrogenated. Polyolefins for use herein can be prepared by the polymerization of $C_4$ to about $C_{14}$ olefinic monomers. Non-limiting examples of olefinic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. In one aspect of the disclosed technology hydrogenated α-olefin monomers include, but are not limited to: 1-hexene to 1-hexadecenes, 1-octene to 1-tetradecene, and mixtures thereof.

Fluorinated or perfluorinated oils are also contemplated within the scope of the disclosed technology. Fluorinated oils include perfluoropolyethers described in European Patent 0 486 135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers.

Other suitable ingredients include, but are not limited to, fatty esters having at least 10 carbon atoms. These fatty esters include esters derived from fatty acids or alcohols (e.g. mono-esters, polyhydric alcohol esters, and di- and tri-carboxylic acid esters). The fatty esters hereof may include or have covalently bonded thereto other compatible functionalities, such as amides and alkoxy moieties (e.g., ethoxy or ether linkages, etc.).

Exemplary fatty esters include, but are not limited to isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the disclosed technology are mono-carboxylic acid esters of the general formula $R^{50}C(O)OR^{51}$, wherein $R^{50}$ and $R^{51}$ are alkyl or alkenyl radicals, and the sum of carbon atoms in $R^{50}$ and $R^{51}$ is at least 10 in one aspect, and at least 22 in another aspect of the disclosed technology.

Still other fatty esters suitable for use in the compositions of the disclosed technology are di- and tri-alkyl and alkenyl esters of carboxylic acids, such as esters of $C_4$-$C_8$ dicarboxylic acids (e.g. $C_1$-$C_{22}$ esters, preferably $C_1$-$C_6$, of succinic acid, glutaric acid, adipic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the compositions of the disclosed technology are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Specific non-limiting examples of suitable synthetic fatty esters for use in the personal cleansing compositions of the disclosed technology include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from ExxonMobil Chemical Company.

Other oily material conditioning agents that are useful in combination with the polymers of the disclosed technology include, for example, acetylated lanolin alcohols; lanolin alcohol concentrates; esters of lanolin fatty acids such as the isopropyl esters of lanolin fatty acid; polyol fatty acids; ethoxylated alcohols, such as ethoxylate and castor oils; sterols; sterol esters; sterol ethoxylates; and like materials.

Preservatives

In one aspect, any preservative suitable for use in personal care can be used in the composition for modifying hair. Suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds as disclosed above (e.g., Polyquaternium-1).

In another aspect, acid based preservatives are useful in the exemplary compositions. The use of acid based preservatives facilitates the formulation of products in the low pH range. Lowering the pH of a formulation inherently provides an inhospitable environment for microbial growth in addition to being suited to the modifying process. Moreover, formulating at low pH enhances the efficacy of acid based preservatives, and affords a personal care product which maintains an acidic pH balance on the skin. Any acid based preservative that is useful in personal care products can be used in the exemplary compositions. In one aspect the acid preservative is a carboxylic acid compound represented by the formula: $R^3C(O)OH$, wherein $R^3$ represents hydrogen, a saturated and unsaturated hydrocarbyl group containing 1 to 8 carbon atoms or $C_6$ to $C_{10}$ aryl. In another aspect, $R^3$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

In another aspect, suitable acids include but are not limited to, oxalic acid, succinic acid, glutaric acid, adipic acid, azelaic acid, maleic acid, fumaric acid, lactic acid, glyceric acid, tartronic acid, malic acid, tartaric acid, gluconic acid, citric acid, ascorbic acid, salicylic acid, phthalic acid, mandelic acid, benzoic acid, benzilic acid, and mixtures thereof.

Salts of the foregoing acids are also useful as long as they retain efficacy at low pH values. Suitable salts include the alkali metal (e.g., sodium, potassium, calcium) and ammonium salts of the acids enumerated above.

The acid based preservatives and/or their salts can be used alone or in combination with non-acidic preservatives typically employed in personal care, home care, health care, and institutional and industrial care products.

The preservatives may comprise from 0.01 wt. % to 3.0 wt. % in one aspect, or from 0.1 wt. % to 1 wt. %, or from 0.3 wt. % to 1 wt. %, of the total weight of the hair modifying composition.

Chelating Agents

Chelating agents can be employed to stabilize the composition against the deleterious effects of metal ions. When utilized, suitable chelating agents include EDTA (ethylene diamine tetraacetic acid) and salts thereof such as disodium EDTA, citric acid and salts thereof, cyclodextrins, and the like, and mixtures thereof.

Such suitable chelating agents can comprise 0.001 wt. % to 3 wt. %, such as 0.01 wt. % to 2 wt. %, or 0.01 wt. % to 1 wt. % of the total weight of the hair modifying composition.

Propellants

Where desired, any known aerosol propellant can be utilized to deliver the hair modifying compositions onto the surface of the hair to be straightened. Exemplary propellants include lower boiling hydrocarbons such as $C_3$-$C_6$ straight and branched chain hydrocarbons. Exemplary hydrocarbon propellants include propane, butane, isobutene, and mixtures thereof. Other suitable propellants include ethers, such as, dimethyl ether, hydrofluorocarbons, such as, 1,1-difluoroethane, and compressed gases, such as air and carbon dioxide.

In one aspect, these compositions can contain from 0.1 wt. % to 60 wt. %, or 0.5 to 35 wt. % propellant, based on the total weight of the composition.

Fragrances and Perfumes

Fragrance and perfume components that may be used in the exemplary composition include natural and synthetic fragrances, perfumes, scents, and essences and any other substances which emit a fragrance. As the natural fragrances, there are those of vegetable origin, such as oil extracts from flowers (e.g., lily, lavender, rose, jasmine, neroli, ylang-ylang), stems and leaves (geranium, patchouli, petitgrain, peppermint), fruits (aniseed, coriander, fennel, needle juniper), fruit skin (bergamot, lemon, orange), roots (mace, angelica, celery, cardamom, costus, iris, sweet flag), woods (pine tree, sandalwood, guaiacum wood, cedar, rosewood, cinnamon), herbs and grasses (tarragon, lemongrass, sage, thyme), needles and twigs (spruce, pine, European red pine, stone pine), and resins and balsam (galbanum, elemi, benzoin, myrrh, frankincense, opopanax), and those of animal origin, such as musk, civet, castoreum, ambergris, or the like, and mixtures thereof.

Examples of synthetic fragrances and perfumes are the aromatic esters, ethers, aldehydes, ketones, alcohols, and hydrocarbons including benzyl acetate, phenoxyethyl isobutylate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styralyl propionate, and benzyl salicylate; benzylethyl ether; straight chain alkanals having 8 to 18 carbon atoms, citral, citronellal, citronellyloxyaldehyde, cyclamen aldehyde, hydroxycitronellal, lilial, and bougeonal; ionone compounds, α-isomethyl ionone, and methyl cedryl ketone; anethole, citronellol, eugenol, isoeugenol, geraniol, lavandulol, nerolidol, linalool, phenylethyl alcohol, and terpineol, alpha-pinene, terpenes (e.g., limonene), and balsams, and mixtures thereof.

Botanicals

Suitable botanical agents useful herein may include, for example, extracts from Echinacea (e.g., sp. angustifolia, purpurea, pallida), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanical extracts may also include, for example, chlorogenic acid, glutathione, glycrrhizin, neohesperidin, quercetin, rutin, morin, myricetin, absinthe, and chamomile.

Hair Fixing Agents

Hair fixing agents may be included in addition to the exemplary thermally-activated agent, including polymer fixatives such as 3-aminopropyl methyl, dimethyl, reaction products of silicones and siloxanes with 2-ethyl-4,5-dihydrooxazole homopolymer, ethyl sulfates, such as Polysilicone-9.

Other commercially available auxiliary hair fixative polymers can be used such as nonionic, cationic, and amphoteric hair setting polymers, cationic conditioning polymers, and combinations thereof. Conventional polymeric hair fixative and hair styling polymers, well known in the art, include natural gums and resins and neutral or anionic polymers of synthetic origin. Listings of commercially available hair fixative and conditioning fixative polymers can be readily found in the INCI Dictionary, in supplier websites, and in the trade literature. See, for example, the Polymer Encyclopedia published in Cosmetics & Toiletries®, 117(12), December 2002 (Allured Publishing Corporation, Carol Stream, Ill.), the relevant disclosures of which are incorporated herein by reference.

Suitable commercially available nonionic polymers (i.e., neutral) used as hair styling or fixative polymers include, without limitation thereto, polyvinylpyrrolidone (PVP), polyvinylpyrrolidone/vinylacetate copolymer (PVP/VA), and the like. Commercially available cationic fixative polymers include, without limitation thereto, polymers having the INCI name, polyquaternium, such as polyquaternium-4, a diallyldimonium chloride/hydroxyethylcellulose copolymer (such as CELQUAT® H-100, Akzo Nobel); polyquaternium-11, a quaternized vinyl pyrrolidone/dimethylaminoethyl methacrylate copolymer (such as GAFQUAT® 734, 755, 755N, ISP); polyquaternium-16, a quaternized vinyl pyrrolidone/vinylimidazolium chloride copolymer (such as LUVIQUAT® FC-370, BASF); polyquaternium-28, a vinylpyrrolidone/methacrylamidopropyltrimethylammonium chloride copolymer (such as GAFQUAT® HS-100, ISP); polyquaternium-46, a quaternized vinylcaprolactam/vinylpyrrolidone/methylvinylimidazolium methosulfate copolymer; polyquaternium-55, a quaternized vinylpyrrolidone/dimethylaminopropylmethylacrylamide/lauryldimethylpropylmethacrylamidoammonium chloride copolymer (such as STYLEZE™ W, ISP), and the like; and amino-substituted polymers which are cationic under acidic pH conditions, such as vinylcaprolactam/PVP/dimethylaminoethylmethacrylate copolymer (such as GAFFIX® VC-713, ISP); PVP/dimethylaminoethylmethacrylate copolymer (such as Copolymer 845, ISP), PVP/DMAPA acrylates copolymer (such as STYLEZE™ CC-10, ISP), the pyrrolidone carboxylic acid salt of chitosan, having the INCI name, Chitosan PCA (such as KYTAMER® PC, Amerchol), and the like.

Suitable amphoteric fixative polymers include, without limitation thereto, octylacryamide/acrylates/butylaminoethylmethacrylate copolymer (such as the AMPHOMER® polymers, Akzo Nobel), acrylates/lauryl acrylate/stearyl acrylate/ethylamine oxide methacrylate copolymers (such as the DIAFORMER® polymers, Clariant Corp.), and the like.

Film-forming polymers such as polyacrylic acid and sodium polyacrylate polymer fixatives, such as Fixate™ RSP available from Lubrizol Advanced Materials, Inc., Cleveland, Ohio, are also suitable fixatives.

The hair fixing agent may be present in the composition at from 0.001 wt. % to 20 wt. %, such as at least 0.1 wt. %, or up to 5 wt. %.

Emollients, Humectants and Emulsifiers

Exemplary emulsifiers include but are not limited to $C_{12}$-$C_{18}$ fatty alcohols; alkoxylated $C_{12}$-$C_{18}$ fatty alcohols; $C_{12}$-$C_{18}$ fatty acids; and alkoxylated $C_{12}$-$C_{18}$ fatty acids, the alkoxylates each having 10 to 30 units of ethylene oxide, propylene oxide, and combinations of ethylene oxide/propylene oxide; $C_8$-$C_{22}$ alkyl mono- and oligoglycosides; ethoxylated sterols; partial esters of polyglycerols; esters and partial esters of polyols having 2 to 6 carbon atoms and saturated and unsaturated fatty acids having 12 to 30 carbon atoms; partial esters of polyglycerols; and organosiloxanes; and combinations thereof.

The fatty alcohols, acids and alkoxylated fatty alcohols and fatty acids are as described in the emollient description above. In one aspect of the disclosed technology, the fatty alcohols and fatty acids each are ethoxylated with 10 to 30 units of ethylene oxide.

The $C_8$-$C_{22}$ alkyl mono- and oligoglycoside emulsifiers are prepared by reacting glucose or an oligosaccharide with primary fatty alcohols having 8 to 22 carbon atoms. Products which are obtainable under the trademark Plantacare® comprise a glucosidically bonded $C_8$-$C_{16}$ alkyl group on an oligoglucoside residue whose average degree of oligomerization is 1 to 2. Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

The partial esters of polyglycerols have 2 to 10 glycerol units and are esterified with 1 to 4 saturated or unsaturated, linear or branched, optionally hydroxylated $C_8$-$C_{30}$ fatty acid residues. Representative partial esters of polyglycerols include diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

The saturated $C_{12}$-$C_{30}$ fatty alcohol emulsifiers are as described in the emollient description set forth above. In one aspect of the disclosed technology, the fatty alcohol emulsifier is selected from but not limited to cetyl alcohol, stearyl alcohol, arachidyl alcohol, behenyl alcohol and lanolin alcohol or mixtures of these alcohols, and as are obtainable in the hydrogenation of unsaturated vegetable oil and animal fatty acids.

The emulsifiers based on the esters and partial esters of polyols having 2 to 6 carbon atoms and linear saturated and unsaturated fatty acids having 12 to 30 carbon atoms are, for example, the monoesters and diesters of glycerol or ethylene glycol or the monoesters of propylene glycol with saturated and unsaturated $C_{12}$-$C_{30}$ fatty acids.

The partially esterified polyglycerol emulsifiers include 2 to about 10 glycerol units and esterified with 1 to 5 saturated or unsaturated, linear or branched, optionally hydroxylated $C_8$-$C_{30}$ fatty acid residues.

In one aspect of the disclosed technology, the emulsifier can be present in an amount ranging from about 0.5 wt. % to about 12 wt. %, from about 1 wt. % to about 15 wt. % in another aspect, and from about 5 wt. % to about 10 wt. % in a further aspect, based on the total weight of the personal care, home care, health care, and institutional care composition in which they are included.

Suitable emollients include but are not limited to an emollient selected from silicone fluids (e.g., volatile silicone oils and non-volatile silicone oils described above); mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; and the like.

Mineral oils and petrolatums include cosmetic, USP and NF grades and are commercially available from Penreco under the Drakeol® and Penreco® trade names. Mineral oil includes hexadecane and paraffin oil.

Suitable fatty alcohol emollients include but are not limited to fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include but are not limited to fatty acids containing 10 to 30 carbon atoms. Exemplary fatty acids are selected from capric acid, lauric acid, myristic acid, palmitic acid, stearic acid, oleic acid, linoleic acid, arachidic acid, behenic acid, and mixtures thereof. Exemplary of the fatty acid and fatty alcohol ester emollients include but are not limited to hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohol emollients are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the disclosed technology, the ethoxylated fatty alcohols can be represented by the formula R'—(OCH$_2$CH$_2$)$_{n'}$—OH, wherein R' represents the aliphatic residue of the parent fatty alcohol and n represents the number of molecules of ethylene oxide. In another aspect of the disclosed technology, R' is derived from a fatty alcohol containing 8 to 30 carbon atoms. In one aspect, n' is an integer ranging from 2 to 50, 3 to 25 in another aspect, and 3 to 10 in a further aspect. In a still further aspect, R' is derived from a fatty alcohol emollient set forth above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the disclosed technology. The ethylene oxide and propylene oxide units of the ethoxylated/propoxylated fatty alcohols can be arranged in random or in blocky order.

More specific examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Alkoxylated fatty acid emollients are formed when a fatty acid is reacted with an alkylene oxide or with a pre-formed polymeric ether. The resulting product may be a monoester, diester, or mixture thereof. Suitable ethoxylated fatty acid ester emollients suitable for use in the disclosed technology are products of the addition of ethylene oxide to fatty acids. The product is a polyethylene oxide ester of a fatty acid. In one aspect of the disclosed technology, the ethoxylated fatty acid esters can be represented by the formula R"—C(O)O(CH$_2$CH$_2$O)$_{n''}$—H, wherein R" represents the aliphatic residue of a fatty acid and n represents the number of molecules of ethylene oxide. In another aspect, n" is an integer ranging from 2 to 50, 3 to 25 in another aspect, and 3 to 10 in a further aspect. In still another aspect of the disclosed technology, R" is derived from a fatty acid containing 8 to 24 carbon atoms. In a still further aspect, R" is derived from a fatty acid emollient set forth above. It is to be recognized that propoxylated and ethoxylated/propoxylated products of the foregoing fatty acids are also contemplated within the scope of the disclosed technology. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like. Guerbet ester emollients are formed from the esterification reaction of a Guerbet alcohol with a carboxylic acid. Guerbet ester emollients are commercially available from the Noveon Consumer Specialties Division of Lubrizol Advanced Materials, Inc. under product designations G-20, G-36, G-38, and G-66. Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from the Lubrizol Advanced Materials, Inc. under the trade names Lanolin LP 108 USP, Lanolin USP AAA, Acetulan™, Ceralan™ Lanocerin™ Lanogel™ (product designations 21 and 41), Lanogene™, Modulan™, Ohlan™, Solulan™ (product designations 16, 75, L-575, 98, and C-24), Vilvanolin™ (product designations C, CAB, L-101, and P). The emollient(s) can be utilized in an amount ranging from about 0.5 wt. % to about 30 wt. % by weight of the total personal care composition in one aspect 0.1 wt. % to 25 wt. % in another aspect, and 5 wt. % to 20 wt. % in a further aspect. While emollients are generally employed in personal care compositions, they can be employed in home care, health care, and institutional care compositions in the same wt. ratios as set forth for personal care compositions so long as they effect a desired physical attribute (e.g., humectant properties) in such compositions.

Suitable humectants include allantoin, pyrrolidonecarboxylic acid and its salts, hyaluronic acid and its salts, sorbic acid and its salts, urea, lysine, arginine, cystine, guanidine, and other amino acids, polyhydroxy alcohols such as glycerin, propylene glycol, hexylene glycol, hexanetriol, ethoxydiglycol, dimethicone copolyol, and sorbitol, and the esters thereof, polyethylene glycol, glycolic acid and glycolate salts (e.g. ammonium and quaternary alkyl ammonium), lactic acid and lactate salts (e.g. ammonium and quaternary alkyl ammonium), sugars and starches, sugar and starch derivatives (e.g. alkoxylated glucose), panthenols such as dl-panthenol, lactamide monoethanolamine, acetamide monoethanolamine, and the like, and mixtures thereof. In one embodiment the humectants include the C$_3$-C$_6$ diols and triols, such as glycerin, propylene glycol, hexylene glycol, hexanetriol, and the like, and mixtures thereof. Such suitable humectants typically comprise about 1 wt. % to about 10 wt. %, preferably about 2 wt. % to about 8 wt. %, and more preferably about 3 wt. % to about 5 wt. % of the total weight of the personal care compositions of the disclosed technology.

Buffer Agents

Buffering agents can be used in the exemplary compositions. Suitable buffering agents include alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

pH Adjusters

The pH of the composition can be from to 1.5-9.5, e.g., at least 2.0, or at least 2.5. In some embodiments, the pH is up to 4.0, or up to 6.5, or up to 8. To provide the selected pH, the composition may include one or more pH modifiers selected from organic and inorganic acids and bases.

The pH of the composition can be adjusted with any combination of acidic and/or basic pH adjusting agents known to the art. Acidic materials include organic acids and inorganic acids, in particular, monocarboxylic acids, dicarboxylic acids, and tricarboxylic acids, for example and not limited to, acetic acid, citric acid, tartaric acid, alpha-hydroxy acids, beta-hydroxy acids, salicylic acid, malic acid, itaconic acid, maleic acid, alginic acid, glutamic acid, galacteric acid, fumaric acid, succinic acid, benzoic acid, etidronic acid, and amino acids (glycine, taurine, alanine, cysteine, cystine, creatine, valine, glutamine, leucine, arginine, lysine, etc.) and natural fruit acids, or inorganic acids, for example, hydrochloric acid, nitric acid, sulfuric acid, sulfamic acid, phosphoric acid, and combinations thereof.

Other acids can be used such as carboxylic acids, such as alpha-hydroxy acid (AHA), beta-hydroxy acid (BHA), alpha-amino acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, alpha-lipoic acid, salicylic acid, AHA salts and derivatives, such as arginine glycolate, ammonium glycolate, sodium glycolate, arginine lactate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited thereto, alpha-amino dicarboxylic acids, such as aspartic acid, glutamic acid, and mixtures thereof, sometimes employed in combination with fruit acid. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some acidic anti-acne actives, for example, can include salicylic acid, derivatives of salicylic acid, such as 5-octanoylsalicylic acid, retinoic acid, and its derivatives.

Basic materials include inorganic and organic bases, and combinations thereof. Examples of inorganic bases include but are not limited to the alkali metal hydroxides (especially sodium, potassium, and ammonium), and alkali metal salts such as sodium borate (borax), sodium phosphate, sodium pyrophosphate, and the like; and mixtures thereof. Examples of organic bases include triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine (2-amino 2-hydroxymethyl-1,3-propanediol), and PEG-15 cocamine.

Such pH modifiers may be present at from 0.0001 wt. % to 50 wt. %, based on the active component.

Particulates and Insoluble Components

Numerous particulate and substantially insoluble compounds and components requiring stabilization and/or suspension can be utilized in the cleansing compositions of the disclosed technology to deliver hair care, skin care and/or aesthetic benefits to the user. The particulate and insoluble components are insoluble in water. By insoluble in water is meant that the solubility in water at 25° C. is 0.01 wt. % or less. Examples of such particulate and insoluble components include, but are not limited to, pigments, exfoliants, anti-dandruff agents, pearlescent agents/opacifiers, and the like.

Pigments

Exemplary pigments are metal compounds or semi metallic compounds and may be used in ionic, nonionic or oxidized form. The pigments can be in this form either individually or in admixture or as individual mixed oxides or mixtures thereof, including mixtures of mixed oxides and pure oxides. Examples are the titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxides, zirconium oxides (e.g., $ZrO_2$), barium sulfate ($BaSO_4$), nylon-12, and mixtures thereof.

Other examples of pigments include thermochromic dyes that change color with temperature, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide nanoparticles, barium oxide, ultramarine blue, bismuth citrate, hydroxyapatite, zirconium silicate, carbon black particles, and the like.

If utilized, the amount of pigment employed in the formulation should be sufficient to provide the desired product aesthetic effect and is well within the skill in the formulation art. In one aspect the amount of pigment typically utilized in the compositions of the disclosed technology range from about 0.5 wt. % to about 20 wt. % in one aspect, from about 1 to about 15 wt. % in another aspect, and from about 5 to about 10 wt. % in a further aspect, based on the total weight of the composition.

Pearlescent/Opacifying Agents

Some formulations are often opacified by deliberately incorporating pearlescent materials therein to achieve a cosmetically attractive pearl-like appearance, known as pearlescence. An opacifier often is included in a composition to mask an undesirable aesthetic property, such as to improve the color of a composition that is darkened due to the presence of a particular ingredient, or to mask the presence of a particulate material in the composition. Opacifiers also are included in aqueous compositions to improve the aesthetics and consumer acceptance of an otherwise esthetically unpleasing composition. For example, an opacifier can impart a pearlescent appearance to a clear composition, thereby communicating an appearance of creaminess, mildness and body to the consumer. Persons skilled in the art are aware of problems faced by formulators in consistently preparing a stable pearlescent formulation. A detailed discussion is found in the article "Opacifiers and pearling agents in shampoos" by Hunting, *Cosmetic and Toiletries*, Vol. 96, pages 65-78 (July 1981), incorporated herein by reference.

The opacifying or pearlescent material includes organic compounds and inorganic compounds. Typical examples of organic compounds are monoesters and/or diesters of ethylene glycol, propylene glycol, diethylene glycol, dipropylene glycol, triethylene glycol or tetraethylene glycol with fatty acids containing from about 6 to about 22 carbon atoms in one aspect, and from about 12 to about 18 carbon atoms in another aspect. Such fatty acids include caproic acid, caprylic acid, 2-ethyhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, erucic acid, and mixtures thereof. In one aspect, ethylene glycol monostearate (EGMS) and/or ethylene glycol distearate (EGDS) and/or polyethylene glycol monostearate (PGMS) and/or polyethyleneglycol distearate (PGDS) are suitable pearlescent agents used in the composition.

Inorganic pearlescent agents include those selected from the group consisting of mica, metal oxide coated mica, silica coated mica, bismuth oxychloride coated mica, bismuth oxychloride, myristyl myristate, glass, metal oxide coated glass, various aluminum and magnesium salts, guanine, fish scales, glitter (polyester or metallic) and mixtures thereof.

Suitable micas include muscovite or potassium aluminum hydroxide fluoride. The platelets of mica are can be coated with a thin layer of metal oxide. Metal oxides are selected from the group consisting of rutile, titanium dioxide, ferric oxide, tin oxide, alumina and mixtures thereof.

A representative listing of opacifiers is found in the CTFA *Cosmetic Ingredient Handbook*, J. Nikitakis, ed., 1988, at page 75. Other pearlescent or opacifying materials are disclosed in U.S. Pat. Nos. 4,654,207; 5,019,376; and 5,384,114; which are herein incorporated by reference.

In one aspect, the amount of the pearlescent or opacifying material can be used in amounts ranging from about 0.01 to about 10 wt. % in one aspect, from about 0.1% to about 5 wt. % in another aspect, and from 0.5 to about 3 wt. % in a further aspect, based upon the total weight of the composition.

Other Insoluble Components

Other generally insoluble components suitable for use in the present compositions, UV absorbers, antibacterial compositions, anti-wrinkling and anti-aging compositions, microsponges, cosmetic beads and flakes. Cosmetic beads, flakes and capsules can be included in a composition for aesthetic appearance or can function as micro- and macro-encapsulants for the delivery of benefit agents to the hair and skin. Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™ and Lipopearl™ microcapsules (Lipo Technologies Inc., Vandalia, Ohio), and Confetti II™ dermal delivery flakes (United-Guardian, Inc., Hauppauge, N.Y.).

Solid Lipid Nanoparticles (SLN, NLC)

Solid lipid nanoparticles (SLN) are a new delivery system for pharmaceutical, cosmetic and/or alimentary active ingredients based on polymeric nanocapsules which contain microemulsions of water in oil (w/o) and which may comprise at least one hydrophilic active ingredient dissolved in the aqueous phase.

A new generation of solid lipid nanoparticles are the nanostructured lipid carriers (NLC). These systems have the same advantages as the SLN, and minimize or avoid some potential problems associated with SLN, such as the low loading capacity and active ingredient expulsion during storage. In contrast to the at least partially crystalline state of the lipid phase in SLN, NLC show a less organized solid lipid matrix. In the case of NLC, there are both solid and liquid compounds in the matrix, thus the greater disorganization leads to the existence of a greater number of holes with the subsequent increase in the ability to encapsulate active ingredients. For the preparation of NLC, sterically very different molecules of lipids are mixed together, mixtures of solid lipids with liquid lipids or oils [Müller, R. H. et al. *Adv. Drug Deliv. Rev.* 54 (Suppl. 1): S131-S155 (2002)].

The SLN and NLC are from 50 to 1000 nm in size and are kept stabilized in an aqueous suspension by surfactants or hydrophilic polymers. The NLC and SLN are very suitable vehicles for releasing active ingredients to the hair and scalp.

In one embodiment, NLC are polymerically coated nanocapsules which contain microemulsions of water in liquid lipids or oils (w/o) and which may comprise at least one hydrophilic active ingredient dissolved in the internal aqueous phase.

The nanocapsules comprise a matrix of liquid lipids or oils and a polymer coating. A w/o microemulsion of at least one hydrophilic active ingredient is incorporated into the lipid matrix. The coating of the nanocapsules constitutes their external part and provides a complete and continuous coating of the inner matrix. The terms liquid lipid and oil are used indistinctly.

The nanocapsules may contain hydrophilic active ingredients incorporated into their interior. The hydrophilic active ingredients incorporated into the nanocapsules can be, without restriction, cosmetic active ingredients and/or adjuvants.

The polymeric coating of the nanocapsules constitutes the external barrier of the nanocapsules; it enables the encapsulation of their components and provides protection for the active ingredients. This increases their stability against chemical degradation by interaction with other possible components of the composition, by hydrolysis and/or by oxidation due to the presence of oxygen and/or light. Furthermore, in the case of hydrophilic active ingredients such as peptides, it avoids the loss of the active ingredient by diffusion towards the external aqueous phase, as often happens in the aqueous dispersions of SLN or NLC.

The preparation procedures of the SLN and NLC nanocapsules are disclosed in U.S. Published Patent Applications 2013/0017239 and 2013/0216596 which are incorporated by reference in their entirety.

In one aspect, the polymer of the polymeric coating of the nanocapsules is selected, without restriction, from the group formed by proteins, polysaccharides, polyesters, polyacrylates, polycyanoacrylates, copolymers and/or mixtures thereof. In one aspect, the polymer of the coating of the nanocapsules is selected from the group formed by gelatin, albumin, soy protein, pea protein, broad bean protein, potato protein, wheat protein, whey protein, β-lactoglobulin, caseinates, wheat starch, corn starch, zein, alginates, carrageenans, pectins, arabinogalactans, gum arabic, xanthan gum, mesquite gum, tragacanth gum, galactomannans, guar gum, carob seed gum, chitosan, agar, poly(L-lysine), dextran sulfate sodium, carboxymethyl galactomannan, carboxymethyl cellulose, methyl cellulose, ethyl cellulose, hydroxypropyl methyl cellulose (HPMC), cellulose nitrate, cellulose acetate butyrate, cellulose acetate phthalate, cellulose hydroxypropyl methyl phthalate, cellulose hydroxypropyl methyl acetate succinate, polyvinyl acetate phthalate, poly (ε-caprolactone), poly(p-dioxanone), poly(δ-valerolactone), poly(β-hydroxybutyrate), poly(β-hydroxybutyrate) and β-hydroxyvalerate copolymers, poly(β-hydroxypropionate), methylacrylic acid copolymers (Eudragit® L and S), dimethylaminoethyl methacrylate copolymers (Eudragit® E), trimethylammonium ethyl methacrylate copolymers (Eudragit® RL and RS), lactic and glycolic acid polymers and copolymers, lactic and glycolic acid polymers and copolymers and polyethylene glycol and mixtures thereof.

Depending on the properties of the polymer used for the polymeric coating of the nanocapsules, it is possible to increase its specificity. A polymer that provides the polymeric coating with a positive charge enables the bond between the nanocapsules and hair or textile materials to be stronger. Optionally, the polymer of the coating of the nanocapsules can be a cationic polymer. The cationic polymer can be a natural or synthetic polymer, for example and not restricted to, cationic derivatives of cellulose, such as quaternized hydroxyethyl cellulose, which can be acquired under the name Polymer JR 400™ by Amerchol; cationic starches; diallyl ammonium and acrylamide salt copolymers; quaternized vinylpyrrolidone/vinylimidazole polymers such as Luviquat™ (BASF); condensation products of polyglycols and amines; polyquaternium polymers and copolymers; polymers called polyquaternium-6, polyquaternium-7, polyquaternium-16, polyquaternium-10 Merquats; polyquaternium-4 copolymers; dicocoylethylhydroxyethylammonium, grafting copolymers with a cellulose skeleton and quaternary ammonium groups; quaternized collagen polypeptides such as laurdimonium hydroxypropyl hydrolyzed collagen (Lamequat™ by GrUnau); quaternized wheat polypeptides; polyethylenimine; cationic silicone polymers such as amidomethicone or quaternium-22 silicone; adipic acid and dimethylamino hydroxypropyl diethylenetriamine copolymers (Cartaretin™ by Sandoz); acrylic acid copolymers with dimethyldiallylammonium chloride (Merquat™ 550 by Chemviron); cationic chitin derivatives such as chitosan and its derivatives; condensation products of cationic dihalogen alkylene such as dibromobutane with bis-dialkylamines; bis-dimethylamino-1,3-propane; derivatives of cationic guar gum such as guar-hydroxypropyltrimonium, Jaguar™ CBS, Jaguar™ C-17, Jaguar™ C-16 by Celanese; quaternary ammonium salt polymers such as Mirapol™ A-15, Mirapol™ AD-1, Mirapol™ AZ-1 by Miranol; quaternized polygalactomanans such as cationic cassia, cationic locus bean gum, cationic tara gum, quaternized polysaccharide polymers of natural derivatives such as azarose; cationic proteins selected from gelatin, gum arabic; cationic polymers from the group formed by polyamides, polycyanoacrylates, polylactides, polyglycolides, polyaniline, polypyrrole, polyvinylpyrrolidone, amino silicone polymers and copolymers, polystyrene, polyvinyl alcohol, polystyrene and maleic acid anhydride copolymers, methyl vinyl ether, epoxy resins and styrene and methyl methacrylate copolymers; dimethylamino methacrylate, cationic polyacrylates and polymethacrylates such as Eudragit™ RL 30 D by Röhm; polyamine derivatives optionally substituted by polyethylene glycol derivatives; polyamino acids under pH conditions wherein they are cationic; polyethyleneimine; quaternized derivatives of polyvinylpyrrolidone (PVP) and hydrophilic urethane polymers, as well as any mixture of the aforementioned cationic groups.

Optionally, the polymer of the coating of the nanocapsules can comprise a plasticizing additive. The plasticizing additive is selected, without restriction, from the group formed by citric acid alkyl esters such as triethyl citrate, tributyl citrate, acetyl tributyl citrate and acetyl triethyl citrate, phthalates such as butyl phthalate and diethyl phthalate, glycerin, sorbitol, maltitol, propylene glycol, polyethylene glycol, glucose, saccharose, lanolin, palmitic acid, oleic acid, stearic acid, fatty acid metal salts such as stearic acid or palmitic acid, sodium stearate, potassium stearate, propylene glycol monostearate, acetylated monoglycerides such as monoacetyl glycerin and glyceryl triacetate or triacetin, glyceryl lecithin, glyceryl monostearate, alkyl sebacates such as dibutyl sebacate or diethyl sebacate, alkyl fumarates, alkyl succinates, medium-chain triglycerides (MCT), castor oil, hydrogenated vegetable oils, waxes and/or mixtures thereof.

Optionally other technical additives of the polymer can be added which improve or facilitate the encapsulation process such as, for example, fluidizers, such as talc, colloidal silicon dioxide, glycerin, polyethylene glycol, glycerin monostearate and/or metal stearate salts.

The term hydrophilic refers to substances which are soluble in water, with a solubility greater than 1 g per 100 ml of water at 20° C. In the disclosed technology, the terms hydrophilic and hydrosoluble are used indistinctly.

The nature of the hydrophilic cosmetic active ingredient and/or adjuvant can be synthetic or natural, or come from a biotechnological procedure or from a combination of a synthetic procedure and a biotechnological procedure. Preferably, the hydrophilic active ingredient of the nanocapsules is thermolabile. A thermolabile active ingredient is understood to be that which presents a degradation equal or greater to 0.5% after having been subjected to a temperature of 80° C. for two hours.

The cosmetic active ingredient is selected, without restriction, from the group formed by amino acids, peptides, proteins, hydrolized proteins, enzymes, hormones, vitamins, mineral salts, nucleotides, nucleic acids, molecules and extracts of biological and biotechnological origin, synthetic or partially synthetic hydrophilic molecules and/or mixtures thereof.

The amino acids, their salts and/or derivatives, as well as the commercial mixtures which contain them, are selected, for example and not restricted to, from the group formed by serine, proline, alanine, glutamate, arginine, glycine, methionine, citrulline, sodium methylglycine diacetate (TRILON® M marketed by BASF), derivatives of amino acids which contain cysteine, in particular N-acetyl cysteine, ergothioneine or S-carboxymethylcysteine, and/or mixtures thereof.

The peptides or the commercial mixtures which contain them are selected, for example and not restricted to, from the group formed by peptides of cosmetic use, such as GHK [INCI: Tripeptide-1], acetyl-glutamyl-methionyl-alanyl-isoleucine, acetyl-arginyl-phenylglycyl-phenylglycine, Bodyfensine™ [INCI: Acetyl Dipeptide-3 Aminohexanoate], Relistase™ [INCI: Acetylarginyltriptophyl Diphenylglycine], acetyl-arginyl-phenylglycyl-valyl-glycine, acetyl-arginyl-phenylglycyl-valyl-phenylglycine, diaminopropionyl-alanyl-asparaginyl-histidine, acetyl-arginyl-asparaginyl-histidyl-citrulline-amide, Aldenine® [INCI: Hydrolized Wheat Protein, Hydrolized Soy Protein, Tripeptide-1], Decorinyl® [INCI: Tripeptide-10 Citrulline], Serilesine® [INCI: hexapeptide-10], Peptide AC29 [INCI: Acetyl Tripeptide-30 Citrulline], Vilastene™ [INCI: Lysine HCl, Lecithin, Tripeptide-10 Citrulline], dGlyage™ [INCI: Lysine HCl, Lecithin, Tripeptide-9 Citrulline], Eyeseryl® [INCI: Acetyl Tetrapeptide-5], Preventhelia® [INCI: Diaminopropionoyl Tripeptide-33], Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Trylagen® [INCI: Pseudoalteromonas Ferment Extract, Hydrolyzed Wheat Protein, Hydrolyzed Soy Protein, Tripeptide-10 Citrulline, Tripeptide-1], Inyline™ [INCI: Acetyl Hexapeptide-30], Melatime™ [INCI: Acetyl Tripeptide-40], Thermostressine™ [INCI: Acetyl Tetrapeptide-22] or Liporeductyl® [INCI: Caffeine, Butcherbroom (*Ruscus Aculeatus*) Root Extract, TEA-Hydroiodide, Carnitine, Ivy (*Hedera Helix*) Extract, Escin, Tripeptide-1] marketed by Lipotec, Matrixyl® [INCI: Palmitoyl Pentapeptide-4], Matrixyl® 3000 [INCI: Palmitoyl Tetrapeptide-7, Palmitoyl Oligopeptide], Dermaxyl® [INCI: Palmitoyl Oligopeptide], Calmosensine™ [INCI: Acetyl Dipeptide-1], Biopeptide CL™ [INCI: Glyceryl Polymethacrylate, Propylene Glycol, Palmitoyl Oligopeptide] or Biopeptide EL™ [INCI: Palmitoyl Oligopeptide] marketed by Sederma, pseudodipeptides, IP 2000 [INCI: Dextran, Trifluoroacetyl Tripeptide-2] marketed by IEB and Atrium, Pepha®-Timp [INCI: Human Oligopeptide-20], ECM-Protect® [INCI: Water (Aqua), Dextran, Tripeptide-2] or Melanostatine®-[INCI: Dextran, Nonapeptide-1] marketed by Atrium Innovations, Timp-Peptide [proposed INCI: Acetyl Hexapeptide], Bronzing S.F. [proposed INCI: Butiryl Pentapeptide], BONT-L-Peptide [INCI: Palmitoyl Hexapeptide-19] or ECM Moduline [proposed INCI: Palmitoyltripeptide] marketed by Infinitec Activos, IP2000 [INCI: Dextran, Trifluoroacetyl tripeptide-2] marketed by Institut Europeen de Biologie Cellulaire, Syn®-Coll [INCI: Palmitoyl Tripeptide-5] marketed by Pentapharm, Neutrazen™ [INCI: Water, Butylene Glycol, Dextran, Palmitoyl Tripeptide-8], ChroNOline™ [INCI: Caprooyl Tetrapeptide-3] or Thymulen-4 [INCI: Acetyl Tetrapeptide-2] marketed by Atrium Innovations/Unipex Group, Meliprene® [INCI: Dextran, Acetyl Heptapeptide-1] or Melitane® [INCI: Acetyl Hexapeptide-1] marketed by Institut Europeen de Biologie Cellulaire/Unipex Group, Skinasensyl™ [INCI: Acetyl Tetrapeptide-15] marketed by Laboratoires Serobiologiques/Cognis, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Syniorage™ [INCI: Acetyl Tetrapeptide-11], Dermican™ [INCI: Acetyl Tetrapeptide-9] marketed by Laboratoires Serobiologiques/Cognis, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Quintescine™ IS [INCI: Dipeptide-4], UCPeptide™ V [INCI: Pentapeptide] or AT Peptide™ IS [INCI: Tripeptide-3] marketed by Vincience/ISP, glutathione, carnosine and/or mixtures thereof; and peptides of pharmaceutical use, such as glucagon, leuprolide, goserelin, triptorelin, buserelin, nafarelin, deslorelin, histrelin, avorelin, abarelix, cetrorelix, ganirelix, degarelix, desmopressin, somatostatin and analogues of somatostatin such as octreotide, vapreotide and lanreotide, among others.

The proteins, hydrolyzed protein, enzymes and hormones, as well as the commercial mixtures which contain them, are selected, for example and not restricted to, from the group formed by Elhibin® [INCI: Glycine Soja (Soybean) Protein], Preregen® [INCI: Glycine Soja (soybean) Protein, Oxido Reductases] or Regu®-Age [INCI:Hydrolyzed Rice Bran Protein, Glycine Soja (Soybean) Protein, Oxido Reductases] marketed by Pentapharm/DSM, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating growth factors, transforming growth factor-beta, tumor necrosis factor-alpha, interferons, interleukins, matrix metalloproteinases, receptor protein tyrosine phosphatases, hydrolyzed vegetable proteins such as hydrolyzed wheat protein, hydrolyzed soy protein or hydrolyzed whey protein, Lipeptide [INCI: Hydrolized vegetable protein] by Lipotec, Collalift® [INCI: Hydrolyzed Malt Extract] marketed by Coletica/Engelhard, Colhibin [INCI: Hydrolyzed Rice Protein] marketed by Pentapharm, Cytokinol® LS [INCI: Hydrolyzed Casein, Hydrolyzed Yeast Protein, Lysine HCL] marketed by Laboratoires Serobiologiques/Cognis, Liftline® [INCI: Hydrolyzed wheat protein] or Ridulisse C® [Hydrolyzed Soy Protein] marketed by Silab, catalase, superoxide dismutase, lactoperoxidase, glutathione peroxidase, lactoprotein, casein, lactoperoxidase, lysozyme, glycosidases, stratum corneum chymotryptic enzyme or SCCE, proteases such as trypsin, chymotrypsin, sutilain, papain or bromelain, DNA repair enzymes such as photolyase or T4 endonuclease V, lipase, luteinizing hormone (LH), follicle-stimulating hormone (FSH), growth hormone, insulin and/or mixtures thereof.

The vitamins are selected, for example and not restricted to, from the group formed by hydrosoluble vitamins, such as vitamin C, vitamin B1, vitamin B2, vitamin B3, vitamin B5, vitamin B6, vitamin B7, vitamin B9, vitamin B12, carnitine and/or mixtures thereof.

The extracts of biological or biotechnological origin, which can be chemically modified, as well as the commercial mixtures which contain them, are selected, for example and not restricted to, from the group formed by vegetable extracts, marine extracts, cell extracts and extracts produced by microorganisms.

The vegetable extracts are selected from the group formed by hydrosoluble vegetable extracts, for example and not restricted to, hydrosoluble extracts of chamomile, ivy, lemon, ginseng, raspberry, Roast amaranth, Rehmannias radix, gardenia, carrot, orange, peach, pineapple, gentian, hibiscus flower, walnut leaf, pumpkin, peony, quinoa, boldo, rough bindweed, salvia, pomegranate, oregano, ginger, marjoram, cranberry, grape, tomato, green tea, black tea, aloe vera (Aloe Barbadensis), Saphora japonica, papaya, pineapple, pumpkin, sweet potato, Bupleurum Chinensis, Cecropia Obtusifolia, Celosia Cristata, Centella Asiatica, Chenopodium Quinoa, Chrysanthellum Indicum, Citrus Aurantium Amara, Coffea Arabica, Coleus Forskohlii, Commiphora Myrrha, Crithmum Maritimum, Eugenia Caryophyllus, Ginkgo Biloba, Hedera Helix (ivy), Hibiscus Sabdariffa, Ilex Paraguariensis, Laminaria Digitata, Nelumbium Speciosum, Paullinia Cupana, Peumus Boldus, Phyllacantha Fibrosa, Prunella Vulgaris, Prunus Amygdalus Dulcis, Ruscus Aculeatus (Butcherbroom extract), Sambucus Nigra, Spirulina Platensis Algae, Uncaria Tomentosa, Verbena Officinalis, Opuntia ficus indica, Salix alba, Lupinus spp., Secale cereale, Tussilago farfara, Achillea millefolium, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifragia sarmentosa, Scutellaria Galericulate, Sedum sarmentosum Bunge, Stellaria medica, Triticum Vulgare, Uva ursi, Whitania somnifera, Aristoloquia clematis, Rosa moschata, Echinacea angustifolia, Symphytum officinale, Equisetum arvense, Hypericum perforatum, Mimosa tenuiflora, Persea gratissima, Prunus africanum, Tormentilla erectea, Solanum tuberosum, Rosmarinus officinalis, Vaccinium angustifolium, Macrocystis pyrifera algae, Padina pavonica, Malpighia punicitolia, Cynara scolymus, Gossypium herbaceum, Panicum miliaceum, Morus nigra, Sesamum indicum, Glycine soja, Triticum vulgare, Glycine Max (soy), malt, flax, red clover, kakkon-to, white lupin, hazelnut, maize, beech tree shoots, Trifolium pratense (red clover), Phormium tenax (New Zealand flax), Cinnamommum zeylanicum, Laminaria saccharina, Spiraea ulmaria, Nettle Root, Pygeum africanum, Avena Sativa, Arnica montana, Cinchona succirubra, Eugenia caryophyllata, Humulus lupulus, Hypericum perforatum, Mentha piperita, Rosmarinus officinalis, Thymus vulgaricus, plant extract of the genus Silybum, extract of legume seeds, extracts of red algae from the genus Porphyra, Phytovityl C® [INCI: Aqua, Zea Mays Extract] marketed by Solabia, Micromerol™ [INCI: Pyrus Malus Extract] or Heather Extract [INCI: Calluna Vulgaris Extract] marketed by Coletica/Engelhard/BASF, Proteasyl® TP LS8657 [INCI: Pisum Sativum Extract] marketed by Laboratoires Serobiologiques/Cognis, Radicaptol [INCI: Propylene Glycol, Water, Passiflora Incarnata Flower Extract, Ribes Nigrum (Blackcurrant) Leaf Extract, Vitis Vinifera (grape) Leaf Extract] marketed by Solabia or ViaPure™ Boswellia [INCI: Olivanum (Boswellia Serrata) Extract] marketed by Soliance, EquiStat [INCI Pyrus Malus Fruit Extract, Glycine Soja Seed Extract] marketed by Coletica/Engelhard, Litchiderm™ [INCI: Litchi Chinensis pericarp extract] or Arganyl™ [INCI: Argania Spinosa Leaf Extract] marketed by Laboratories Serobiologiques/Cognis, Dakaline [INCI: Prunus amygdalus dulcis, Anogeissus leiocarpus bark extract] marketed by Soliance, Actimp 1.9.3® [INCI: Hydrolyzed Lupine Protein] marketed by Expanscience Laboratorios, Pronalen® Refirming HSC [INCI: Triticum vulgare, Silybum Marianum, Glycine Soy, Equisetum Arvense, Alchemilla Vulgaris, Medicago Sativa, Raphanus Sativus] or Polyplant® Refirming [INCI: Coneflower, Asiatic Centella, Fucus, Fenugreek] marketed by Provital, Lanablue® [INCI: Sorbitol, Algae Extract] marketed by Atrium Innovations, Firmiderm® L59120 [INCI: Terminalia Catappa Leaf extract, Sambucus Negra Flower Extract, PVP, Tannic Acid] marketed by Laboratoires Serobiologiques/Cognis, among others.

Cell extracts and extracts produced by microorganisms, or commercial mixtures which contain them, are selected from the group formed by hydrosoluble cell extracts and hydrosoluble extracts produced by microorganisms, for example and not restricted to, Antarcticine® [INCI: Pseudoalteromonas Ferment Extract] and Trylagen® [INCI: Pseudoalteromonas Ferment Extract, Hydrolyzed Wheat Protein, Hydrolyzed Soy Protein, Tripeptide-10 Citrulline, Tripeptide-1] marketed by Lipotec, yeast extract, extract of Saccharomyces cerivisiae and the product of milk fermentation with Lactobacillus Bulgaricus, among others.

The amount of active ingredient contained in the delivery system ranges between 0.00001 and 50% in weight, preferably between 0.0001 and 40% in weight, and more preferably between 0.001 and 30% in weight.

The nanocapsules comprise other cosmetic and/or active ingredients and/or adjuvants of any nature, hydrophobes, hydrophiles and amphiphiles, which can be found inside the nanocapsules in solution or in suspension in the lipid matrix, or in the aqueous phase of the microemulsion. In particular, the cosmetic and/or alimentary active ingredients and/or adjuvants are selected, for example and not restricted to, from the group formed by surfactants, humectants or substances which retain moisture, moisturizers or emollients, agents stimulating healing, coadjuvant healing agents, agents stimulating re-epithelialization, coadjuvant re-epithelialization agents, agents which synthesize dermal or epidermal macromolecules, firming and/or redensifying and/or restructuring agents, cytokine growth factors, agents which act on capillary circulation and/or microcirculation, anti-glycation agents, free radical scavengers and/or anti-atmospheric pollution agents, reactive carbonyl species scavengers, 5α-reductase-inhibiting agents, lysyl- and/or prolyl hydroxylase inhibiting agents, defensin synthesis-stimulating agents, bactericidal agents and/or bacteriostatic agents and/or antimicrobial agents and/or germicidal agents and/or fungicidal agents and/or fungistatic agents and/or germ-inhibiting agents, anti-viral agents, antiparasitic agents, anti-histaminic agents, NO-synthase inhibiting agents, desquamating agents or keratolytic agents and/or exfoliating agents, comedolytic agents, anti-psoriasis agents, anti-dandruff agents, anti-inflammatory agents and/or analgesics, anesthetic agents, anti-wrinkle and/or anti-aging agents, cosmetic and/or absorbent and/or body odor masking deodorants, antiperspirant agents, perfuming substances and/or perfumed oils and/or isolated aromatic compounds, anti-oxidizing agents, agents inhibiting vascular permeability, hydrolytic epidermal enzymes, whitening or skin depigmenting agents, agents inhibiting sweat-degrading enzymes, agents capable of filtering UV rays, agents which stimulate or regulate keratinocyte differentiation, anti-itching agents, agents which stimulate or inhibit the synthesis of melanin, propigmenting agents, self-tanning agents, melanocyte proliferation stimulating agent, liquid propellants, vitamins, amino acids, proteins, biopolymers, gelling polymers, skin relaxant agents, agents capable of reducing or treating bags under eyes, agents for the treatment and/or care of sensitive skin, astringent agents, agents regulating sebum production, anti-stretch mark agents, lipolytic agents or agents stimulating lipolysis, venotonic agents, anti-cellulite agents, calming agents, agents acting on cell metabolism, agents to improve dermal-epidermal junction, agents inducing hair growth or hair-loss retardants, body hair growth inhibiting or retardant agents, heat shock protein synthesis stimulating agents, muscle relaxants, muscle contraction inhibitory agents, agents inhibiting acetylcholine receptor clustering, anticholinergic agents, elastase inhibitory agents, matrix metalloproteinase inhibitory agents, chelating agents, vegetable extracts, essential oils, marine extracts, mineral salts, cell extracts, emulsifying agents, agents stimulating the synthesis of lipids and components of the stratum corneum (ceramides, fatty acids, etc.), agents obtained from a bio-fermentation process and/or mixtures thereof. The nature of these active ingredients and/or cosmetic and/or alimentary adjuvants can be synthetic or natural, such as vegetable extracts, or come from a biotechnological process or from a combination of a synthetic process and a biotechnological process. Additional examples can be found in the *CTFA International Cosmetic Ingredient Dictionary & Handbook,* 12th Edition (2008). In the context of the disclosed technology, a biotechnological process is understood to be any process which produces the active ingredient, or part of it, in an organism, or in a part of it.

The humectant or substance that retains moisture, moisturizer or emollient is selected, for example and not restricted to, from the group formed by polyols and polyethers such as glycerin, ethylhexylglycerin, caprylyl glycol, pentylene glycol, propylene glycol and their derivatives, Glycereth-26, Sorbeth-30; panthenol; pyroglutamic acid and its salts and derivatives; amino acids, such as serine, proline, alanine, glutamate or arginine; ectoine and its derivatives; N-(2-hydroxyethyl)acetamide; N-lauroyl-pyrrolidone carboxylic acid; N-lauroyl-L-lysine; N-alpha-benzoyl-L-arginine; urea; creatine; α- and β-hydroxy acids such as lactic acid, glycolic acid, malic acid, citric acid or salicylic acid, and their salts; polyglyceryl acrylate; sodium glucuronate, carraghenates (*Chondrus crispus*) or chitosan; glycosaminoglycans such as hyaluronic acid and derivatives thereof; aloe vera in any of its forms; honey; soluble collagen; lecithin and phosphatidylcholine; ceramides; cholesterol and its esters; tocopherol and its esters, such as tocopheryl acetate or tocopheryl linoleate; long-chain alcohols such as cetearyl alcohol, stearyl alcohol, cetyl alcohol, oleyl alcohol, isocetyl alcohol or octadecan-2-ol; long-chain alcohol esters such as lauryl lactate, myristyl lactate or $C_{12}$-$C_{15}$ alkyl benzoates; fatty acids such as stearic acid, isostearic acid or palmytic acid; polyunsaturated fatty acids (PUFAs); sorbitans such as sorbitan distearate; glycerides such as glyceryl monoricinoleate, glyceryl monostearate, glyceryl stearate citrate or caprylic and capric acid triglyceride; saccarose esters such as saccarose palmitate or saccarose oleate; butylene glycol esters, such as dicaprylate and dicaprate; fatty acid esters such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® [INCI: Pseudoalteromonas Ferment Extract] or acetyl-glutamyl-methionyl-alanyl-isoleucine, acetyl-arginyl-phenylglycyl-phenylglycine or acetyl-arginyl-6-aminohexanoyl-alanine marketed by Lipotec, petrolatum; mineral oil; mineral and synthetic waxes; beeswax (cera alba); paraffin; or waxes and oils with vegetable origins such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose oil (*Rosa moschata*), soya bean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), and/or mixtures thereof, among others.

The bactericidal and/or bacteriostatic agent and/or antimicrobial and/or germicidal agent and/or fungicidal agent and/or fungistatic agent and/or germ inhibiting agent is selected, for example and not restricted to, from the group formed by macrolides, pyranosides, calcium channel blockers, for example and not restricted to, cinnarizine and diltiazem; hormones, for example and not restricted to, estril, analogues thereof or thyroxine and/or its salts, caprylyl glycol, imidazolidinyl urea, methyl 4-hydroxybenzoate

[INCI: methylparaben], ethyl 4-hydroxybenzoate [INCI: ethylparaben], propyl 4-hydroxybenzoate [INCI: propylparaben], butyl 4-hydroxybenzoate [INCI: butylparaben], isobutyl 4-hydroxybenzoate [INCI: isobutylparaben], 1,3-bis(hydroxymethyl)-5,5-dimethylimidazolidine-2,4-dione [INCI: DMDM Hydantoin], benzyl 4-hydroxybenzoate [INCI: benzylparaben], benzyl alcohol, dehydroacetic acid, benzoic acid, sorbic acid, salicylic acid, formic acid, propionic acid, 2-bromo-2-nitropropane-1,3-diol, 3-p-chlorophenoxy-1,2-propanodiol [INCI: chlorphenesin], dichlorobenzyl alcohol, iodopropynyl butylcarbamate, benzalkonium chloride, odor-absorbing fungicides such as zinc ricinoleate, cyclodextrins, benzethonium chloride, chlorhexidine, ethanol, propanol, 1,3-butanediol, 1,2-propylene glycol, undecylenic acid, dehydroacetic acid, N-methylmorpholine acetonitrile (MMA), isopropanol, methanol, 1,2-hexanediol, 1,2-octanediol, pentylene glycol, glycerin laurate, glycerin caprilate, glycerin caprate, benzoyl peroxide, chlorhexidine gluconate, triclosan and derivatives thereof, phenoxyethanol, terpinen-4-ol, α-terpineol, resorcinol, stiemycin, erythromycin, neomycin, clindamycin and its esters, tetracyclines, metronidazole, azelaic acid, tolnaftate, nystatin, clotrimazole, ketoconazole, derivatives of zinc such as zinc piritionate or trithionate, zinc oxide and zinc undecylenate, piroctone olamine, isothiazolinones, selenium sulfur, benzyl hemiformal, boric acid, sodium borate, 6,6-dibromo-4,4-dichloro-2,2'-methylenediphenol [INCI: bromochlorophene], 5-bromo-5-nitro-1,3-dioxane, tosylchloramide sodium [INCI: chloramine T], chloroacetam ide, p-chloro-m-cresol, 2-benzyl-4-chlorophenol [INCI: chlorophene], dimethyl oxazolidine, dodecyl dimethyl-2-phenoxyethyl ammonium bromide [INCI: domiphen bromide], 7-ethyl bicyclooxazolidine, hexetidine, glutaraldehyde, N-(4-chlorophenyl)-N-[4-chloro-3-(trifluoromethyl)phenyl]-urea [INCI: cloflucarban], 2-hydroxy-4-isopropyl-2,4,6-cycloheptatriene-1-one [INCI: Hinokitiol], isopropylmethylphenol, mercury salts, aluminum salts, nisin, phenoxyisopropanol, o-phenylphenol, 3-heptyl-2-[(3-heptyl-4-methyl-3H-thiazole-2-ylidene)methyl]-4-methylthiazole iodide [INCI: Quaternium-73], silver chloride, sodium iodide, thymol, undecylenic acid, diethylenetriaminepentaacetic acid, ethylenediaminetetraacetic acid and ethylenediaminetetraacetates, lactoperoxidase, glucose oxidase, lactoferrin, alkylaryl sulfonates, halogenated phenols, phenol mercury acetate and/or mixtures thereof, benzamidines, isothiazolines, derivatives of phthalimide, derivatives of pyridine, guanidines, quinolines, 1,2-dibromo-2,4-dicyanobutane, iodine-2-propylbutyl carbamate, iodine, tamed iodines, peroxo compounds, 4-chloro-3,5-dimethylphenol, 2,2'-methylene-bis(6-bromo-4-chlorophenol), 3-methyl-4-(1-methylethyl)phenol, 3-(4-chlorophenoxy)-1,2-propanediol, 3,4,4'-trichlorocarbanilide (TTC), thiamine essence, eugenol, farnesol, glycerin monolaurate, diglycerin monocaprinate, N-alkyl salicylic acid amides such as n-octyl salicylic acid amide or n-decyl salicylic acid amide, derivatives of halogenated xylene and cresol, such as p-chloro-meta-cresol or p-chloro-meta-xylene, extracts of *Allium sativum, Calendula officinalis, Chamomilla recutita, Echinacea Purpura, Hyssopus Officinalis, Melaleuca altemifolia* or tea tree oil, carnation essence, menthol and mint essence, among others.

The hair growth inducing agent, the agent which acts on capillary circulation and/or microcirculation, or the hair loss retardant agent is selected, for example and not restricted to, from the group formed by the extracts of *Tussilago farfara* or *Achillea millefolium*, nicotinic acid esters such as $C_3$-$C_6$ alkyl nicotinates such as methyl or hexyl nicotinate, benzyl nicotinate, or tocopheryl nicotinate; biotin, 5α-reductase-inhibiting agents, anti-inflammatory agents, retinoids, for example and not restricted to, all-trans-retinoic acid or tretinoin, isotretinoin, retinol or vitamin A, and derivatives thereof, such as zinc salt of acetate, palmitate, propionate, motretinide, etretinate and trans-retinoate; anti-bacterial agents, calcium channel blockers, for example and not restricted to, cinnarizine and diltiazem; hormones, for example and not restricted to, estriol, its analogues or thyroxine, its analogues and/or salts; antiandrogenic agents, for example and not restricted to, oxendolone, spironolactone or diethylstilbestrol; anti-radical agents, esterified oligosaccharides, for example and not restricted to, those described in documents EP 0 211 610 and EP 0 064 012; derivatives of hexosaccharic acids, for example and not restricted to, glucosaccharic acid or those described in document EP 0 375 388; glucosidase inhibitors, for example and not restricted to, D-glucaro-1,5-lactam or those described in document EP 0 334 586; glycosaminoglycanase and proteoglycanase inhibitors, for example and not restricted to L-galactono-1,4-lactone or those described in document EP 0 277 428; tyrosine kinase inhibitors, for example and not restricted to, 1-amido-1-cyano(3,4-dihydroxyphenyl)ethylene or those described in document EP 0403238, diazoxides, for example and not restricted to, 7-(acetylthio)-4',5'-dihydrospiro[androst-4-ene-17,2'-(3H) furan]-3-one, 1,1-dioxide of 3-methyl-7-chloro[2H]-1,2,4-benzothiadiazine or spirooxazine; phospholipids, for example and not restricted to, lecithin; salicylic acid and derivatives thereof, hydroxycarboxylic or keto carboxylic acids and esters thereof, lactones and their salts; anthralin, eicosa-5,8,11-trienoic acids and esters thereof or amides among others, minoxidil and derivatives or mixtures thereof.

The antioxidant is selected, for example and not restricted to, from the group formed by butylhydroxytoluene (BHT), butylhydroxyanisole (BHA), tert-butylhydroquinone (TBHQ), 2,6,-di-tert-butyl-4-methylphenol, gallic acid esters such as propyl gallate, probucol, polyphenoles, ascorbic acid and its salts, enzymes such as catalase, superoxide dismutase and peroxidases; citric acid, citrates, monoglyceride esters, calcium metabisulfate, lactic acid, malic acid, succinic acid, tartaric acid, vitamin A or β-carotene, vitamins E and C, tocopherols such as vitamin E acetate, ascorbic acid esters such as ascorbyl palmitate and ascorbyl acetate, zinc, copper, mannitol, reduced glutathione, carotenoids such as cryptoxanthin, astaxanthin and lycopene; cysteine, uric acid, carnitine, taurine, tyrosine, lutein, zeaxanthin, N-acetylcysteine, carnosine, γ-glutamylcysteine, quercetin, lactoferrin, dihydrolipoic acid, tea catechins, retinyl palmitate and derivatives thereof, bisulfate, metabisulfite and sodium sulfite, chromans, chromens and their analogues, Lipochroman-6 [INCI: Dimethylmethoxy Chromanol], chelating agents of metals such as EDTA, sorbitol, phosphoric acid or dGlyage™ [INCI: Lysine HCl, Lecithin, Tripeptide-9 Citrulline]; extract of *Ginkgo Biloba*, plant extracts such as sage, pomegranate, rosemary, oregano, ginger, marjoram, cranberry, grape, tomato, green tea or black tea; oleoresin extract, extract of plants which contain phenols such as vanillin, ellagic acid and resveratrol; tertiary butylhydroquinone or mixtures thereof, metal salts with a valence of 2 such as selenium, cadmium, vanadium or zinc; α-lipoic acid, coenzyme Q, idebenone or derivatives thereof.

The agent capable of filtering UV rays is selected, for example and not restricted to, from the group formed by organic or mineral photoprotective agents active against A and/or B ultraviolet rays such as substituted benzotriazoles, substituted diphenylacrylates, organic nickel complexes, umbelliferone, urocanic acid, biphenyl derivatives, stilbene, 3-benzylidene camphor, and derivatives thereof such as 3-(4-methylbenzylidene)camphor; derivatives of 4-aminobenzoic acid, 2-ethylhexyl 4-(dimethylamino)benzoate, 2-octyl 4-(dimethylamino)benzoate and amyl 4-(dimethylamino)benzoate; cinnamic acid esters, such as 2-ethylhexyl 4-methoxycinnamate or diethylamino hydroxybenzoyl hexyl benzoate, propyl 4-methoxycinnamate, isoamyl 4-methoxycinnamate, 2-ethylhexyl (octocrylenes) 2-cyano-3,3-phenyl cinnamate; salicylic acid esters, such as 2-ethylhexyl salicylate, 4-isopropylbenzyl salicylate, homomenthyl salicylate; benzophenone derivatives, such as 2-hydroxy-4-methoxybenzophenone, 2-hydroxy-4-methoxy-4'-methylbenzophenone, 2,2'-dihydroxy-4-methoxybenzophenone; benzalmalonic acid esters, such as di-2-ethylhexyl 4-methoxybenzalmalonate; triazine derivatives, such as 2,4,6-trianilino, p-carbo-2'-ethyl-1'-hexyloxy-1,3,5-triazine, octyl triazone or dioctyl butamido triazones; propane-1,3-diones, such as 1-(4-tert-butylphenyl)-3-(4'-methoxyphenyl) propane-1,3-dione; ketotricyclo(5.2.1.0)decane derivatives; 2-phenylbenzimidazole-5-sulfonic acid; benzophenone sulfonic acid derivatives, such as 2-hydroxy-4-methoxybenzophenone-5-sulfonic acid and its salts; 4-(2-oxo-3-bornylidenemethyl)benzenesulfonic acid, benzoyl methane derivatives, such as benzoyl methane 2-methyl-5-(2-oxo-3-bornylidene)sulfonic acid, such as 1-(4'-tert-butylphenyl)-3-(4'-methoxyphenyl)propane-1, 3-dione, 4-tert-butyl-4'-methoxydibenzoylmethane, 1-phenyl-3-(4'-isopropylphenyl)-propane-1,3-dione, enamine compounds, anthranilates, silicons, benzimidazole derivatives, imidazolines, benzoyl derivatives, Chromabright™ [INCI: Dimethylmethoxy Chromanyl Palmitate] or Preventhelia® [INCI: Diaminopropionoyl Tripeptide-33] both marketed by Lipotec, metal oxides such as zinc oxide, titanium, iron, zirconium, silicon, manganese, aluminum and cerium; silicates, talc, barium sulfate, zinc stearate, carbon nanotubes and/or mixtures thereof.

If utilized, the amount of the SLN and/or NLC, as well as other insoluble components employed in the formulation should be sufficient to provide the desired product benefit and/or aesthetic effect and is well within the skill in the formulation art. In one aspect the amount of these components typically utilized in the compositions of the disclosed technology can range from about 0.05 wt. % to about 25 wt. %, or from about 0.5 to about 20 wt. %, or from about 1 to about 10 wt. %, based on the total weight of the composition.

The following examples further describe and demonstrate embodiments within the scope of the present technology. These examples are presented solely for illustration, and are not to be construed as limitations of the present technology since many variations thereof are possible without departing from the spirit and scope thereof. Unless otherwise specified weight percent (wt. %) is given in weight percent, based on the weight of the total composition.

Exemplary Cream Formulations

Cream formulations may be formulated as shown below.

| Component | Example 1 (wt. % actives) | Example 2 (wt. % actives) |
|---|---|---|
| Propylene carbonate + Glycol | 16-35 | 17-25 |
| Propylene carbonate/Glycol | 0.5-3.5 | 0.5-3.5 |
| Rheology modifier | 0-20 | 1-10 |
| pH modifier (in an amount sufficient to provide a pH of up to 8.5) | 0.01-10 | 0.02-5 |
| Preservative | 0-2 | 0.01-1 |
| Organic solvent | 0-50 | 0.2-30 |
| Other components | 0-20 | 0-10 |
| Water | q.s. to 100% | q.s. to 100% |

As will be appreciated, compositions can be formed by combining ranges from Examples 1 and 2. Additionally, the selected process, such as contact time and heating temperature, may also influence the selection of the composition components and their amounts, as demonstrated by the examples below.

Results of tests suggest that propylene carbonate in combination with certain glycols in certain concentrations, can readily penetrate the hair fibers and react with hard proteinaceous materials via a flat iron at a temperature of about 150° C. or such as about 210° C. The curly hair-tresses used in the tests, once straightened, can withstand up to 20 shampoo wash cycles. The straightened hair-tresses look shiny and feel smooth and silky without malodor.

EXAMPLES

In the following examples, the hair type and curliness is based on the definition published by L'Oreal (Roland de la Mettrie, et al. "Shape Variability and Classification of Human Hair: A Worldwide Approach," Human Biology, June 2007). This assigns a number to the hair from I-VIII, with I being the straightest and VIII representing dense, very curly hair. In general, the samples used herein were curly, classed as type 4-5. After thermal modifying, the hair-tress typically becomes type I. However, the hair relaxes on washing. If, after 3-shampoo-wash-cycle, the hair-tress relaxes to type 3-4, this can be considered as inefficiently straightened (relaxed).

To simulate human hair on the head, curly Brazilian hair tresses were obtained from International Hair Importer and Product Inc. Each single hair-tress is about 2.5 g in weight and has approximate dimensions of 20 cm in length and 10 cm in width at the widest point. The tresses are each clamped at the root end.

Prior to use, each virgin dark brown curly hair-tress was shampooed by using a commercial clarifying shampoo (VO5™ or Suave™ shampoo) by gently massaging for 30 seconds followed by rinsing for 60 seconds with running warm water (35-38° C.). Each washed hair-tress is then dried at room temperature under 30-50% RH conditions.

Two different application methods were evaluated:

A. Solution-Dipping

Typically, a solution of the propylene carbonate/glycol hair care component is prepared in a suitable solvent system. The hair tress is immersed completely in the solution with controlled concentration of candidate hair care component, pH, temperature and soaking time, such as for up to 30 minutes or up to 60 minutes. Then, the hair tress is removed from the solution, excess amount of material squeezed out, and the tress is blow-dried to at least 95% dryness before thermal modifying with a flat iron.

B. Hair Application

Another method is to apply 2.5 g of the formulation containing the propylene carbonate/glycol component on a dry cleaned 2 g curly hair tress and allowed to soak for up to 30 minutes or up to 60 minutes. After the controlled application time, the hair tress is blow-dried to at least 95% of dryness before thermal modifying process with a flat iron.

Thermal Modification Procedure

For thermal modification by flatiron, a commercial flat iron, sold under the tradename Nano Titanium™ by BaByliss PRO was used. The protocol used was the following:
1. The flat iron is set at targeted temperature (210° C.).
2. The heated flat iron is drawn from the top to the bottom of the tress at a glide speed of 5 cm/sec.
3. The thermal process is repeated for 10 passes.

After the thermal straightening treatment, the hair-tress is allowed to cool down to the room temperature.

Wash Fastness

The shampoo wash cycle is carried out by applying 0.5 g shampoo (VO5® or Suave® shampoo) on the hair tress which weighs approximately 2 g. The shampoo is massaged into the hair tress with the fingers for 30 seconds followed by rinsing for 60 seconds with running warm water (32-35° C.). The washed hair tress is then dried at ambient room conditions (23° C. at 50% RH). Consecutive shampoo wash cycles are carried out without the drying step. The examination of thermally straightened hair tresses is performed by visually examining a tress which has been treated with the hair care composition for 30 minutes, flat ironed at 210° C. (glide speed: 5 cm·sec.; 10 passes). Typically, the hair tress is straight. After three consecutive wash cycles, the hair tress is dried in ambient room conditions (23° C. and 50% RH) and again visually evaluated for final appearance. Tresses treated with compositions exhibiting "slight curl reversion" and "curl reversion" fail, and such compositions are considered not to be an effective straightener. Tresses treated with compositions that exhibit "no curl reversion" pass and are considered to be effective straighteners. The hair tresses depicted in FIG. 1 illustrates the pass/fail criteria (D, D' and E are failures; C passes).

Sensory Panel Testing of Conditioning Attributes

Various treatment compositions are compared by a trained panel (at least 3 panelists) for the evaluation of conditioning attributes of the compostions of the present technology using a forced choice test design between two treated hair tresses. Each panelist is asked to indicate which tress performs better for each of 4 sensory attributes evaluated in comparing the two test formulations on the treated hair tresses. The sensory attributes evaluated by the panel include: (1) ease of wet combing; (2) wet feel (slippery feel or wet conditioned feel); (3) ease of dry combing; and (4) dry feel (soft feel or dry conditioned feel). The test protocol utilizes a matrix design of 6 treated tresses (3 replicates for each test formulation). The test matrix allows for the direct blind comparison of the 3 replicate treated tresses with treatment A versus 3 replicate treated tresses treated with comparative treatment B. By permutation of the 3 replicate treatments for each of the test formulations (disclosed technology and comparative), nine comparisons of paired tresses (disclosed technology formulation versus comparative formulation) are possible. The matrix is designed such that duplicate evaluations are included from the panel members. A total of 36 comparisons are carried out with the matrix design.

Results

Tables 1-6 show the results obtained with various formulation compositions on Brazilian type III hair tresses treated with the dipping method, unless specified otherwise, according to the procedures previously described.

TABLE 1

Blends of Propylene Carbonate/Propylene Glycol

| Ex. | PC + PG (wt %) | PC (wt %) | Glycol (wt %) PG | Solvent (wt %) D.I. Water | Hair tress appearance After Flat Ironing | After 3 Washes |
|---|---|---|---|---|---|---|
| 1[1] | 15 | 5 | 10 | 85 | Straight | Curl Reversion* |
| 2 | 17.5 | 7.5 | 10 | 82.5 | Straight | Straight (no curl reversion) |
| 3 | 20 | 10 | 10 | 80 | Straight | Straight (no curl reversion) |
| 4[1] | 10 | 6 | 4 | 90 | Straight | Curl Reversion |
| 5[1] | 15 | 6 | 9 | 85 | Straight | Slight Curl Reversion |
| 6 | 17.5 | 6.65 | 10.85 | 82.5 | Straight | Straight (no curl reversion) |
| 7[1] | 0 | 0 | 10.85 | 89.25 | Straight | Curl Reversion |
| 8 | 17.5 | 10.85 | 6.65 | 82.5 | Straight | Straight (no curl reversion) |
| 9[1] | 10.85 | 10.85 | 0 | 89.25 | Straight | Slight Curl Reversion |
| 10 | 20 | 8 | 12 | 80 | Straight | Straight (no curl reversion) |
| 11 | 20 | 12 | 8 | 80 | Straight | Straight (no curl reversion) |
| 12 | 20 | 15 | 5 | 80 | Straight | Straight (no curl reversion) |
| 13[1] | 15 | 9 | 6 | 80 | Straight | Slight Curl Reversion |
| 14[1] | 30 | 30 | 0 | 70 | Straight | Slight Curl Reversion |
| 15[1] | 100 | 100 | 0 | 0 | Straight | Curl Reversion |
| 16[1] | 100 | 5 | 95 | 0 | Straight | Curl Reversion |
| 17[1] | 100 | 10 | 90 | 0 | Straight | Curl Reversion |

[1]Comparative
*Curl reversion after 1 wash
PG = propylene glycol (1,2-propane diol)
PC = propylene carbonate
D.I. = deionized

TABLE 2

Blends of Propylene Carbonate/Non-Glycol Adjuvant

| Ex. | PC + Adjuvant (wt %) | PC (wt %) | Adjuvant (wt %) | Solvent (wt %) D.I. Water | Hair tress appearance After Flat Ironing | After 5 Washes |
|---|---|---|---|---|---|---|
| 18[1] | 17.5 | 7.5 | Ethanol (10) | 82.5 | Straight | Curl Reversion |
| 19[1] | 17.5 | 7.5 | Dodecenol (10) | 82.5 | Straight | Curl Reversion |

[1]Comparative
PC = propylene carbonate
D.I. = deionized

TABLE 3

Blends with Propylene Carbonate/Propylene Glycol and Acids

| | PC + | | | D.I. | | | Hair tress appearance | |
|---|---|---|---|---|---|---|---|---|
| Ex. | PG (wt %) | PC (wt %) | PG (wt %) | Water (wt %) | pH Adjuster | pH | After Flat Ironing | After 5 Washes |
| 20 | 17.5 | 7.5 | 10 | 85 | Itaconic Acid[1] | 2.74 | Straight | Straight (no curl reversion) |
| 21 | 17.5 | 7.5 | 10 | 82.5 | Maleic Acid[1] | 2.14 | Straight | Straight (no curl reversion) |
| 22 | 17.5 | 7.5 | 10 | 82.5 | Citric Acid[1] | 2.45 | Straight | Straight (no curl reversion) |
| 23 | 17.5 | 7.5 | 10 | 82.5 | Glycolic Acid[1] | 2.50 | Straight | Straight (no curl reversion) |
| 24 | 17.5 | 7.5 | 10 | 82.5 | Lactic Acid[1] | 3.10 | Straight | Straight (no curl reversion) |
| 25 | 17.5 | 7.5 | 10 | 82.5 | Alginic Acid[1] | 2.65 | Straight | Straight (no curl reversion) |
| 26 | 17.5 | 7.5 | 10 | 82.5 | Succinic Acid[1] | 2.70 | Straight | Straight (no curl reversion) |
| 27 | 17.5 | 7.5 | 10 | 82.5 | Acetic Acid[1] | 3.5 | Straight | Straight (no curl reversion) |
| 28 | 17.5 | 7.5 | 10 | 82.5 | Tartaric Acid[1] | 2.90 | Straight | Straight (no curl reversion) |

PC = propylene carbonate
PG = propylene glycol (1,2-propane diol)
[1]Acid amount: 1.5 wt %

Brown Brazilian type III hair tresses were treated with the following formulations according to the direct hair application procedure previously described.

TABLE 4

Blends with Propylene Carbonate/1,3-Propane Diol and Acids

| | PC + | | | D.I. | | | Hair tress appearance | |
|---|---|---|---|---|---|---|---|---|
| Ex. | PD13 (wt %) | PC (wt %) | PD13 (wt %) | Water (wt %) | pH adjuster | pH | After Flat Ironing | After 5 Washes |
| 29 | 17.5 | 7.5 | 10 | 82.5 | Citric Acid[1] | 2.45 | Straight | Straight (no curl reversion) |
| 30 | 17.5 | 7.5 | 10 | 82.5 | Glycolic Acid[1] | 2.75 | Straight | Straight (no curl reversion) |
| 31 | 30 | 12.9 | 17.1 | 70 | Citric Acid[1] | 2.40 | Straight | Straight (no curl reversion) |
| 32 | 30 | 12.9 | 17.1 | 70 | Glycolic Acid[1] | 2.70 | Straight | Straight (no curl reversion) |
| 33 | 17.5 | 7.5 | 10 | 82.5 | None | 5.50 | Straight | Straight (no curl reversion) |

PD13 = 1,3-propane diol
PC = propylene carbonate
[1]Acid amount: 1.5 wt %

TABLE 5

Addition of NLC

|  | Example 34 | Example 35 |
| --- | --- | --- |
| D.I. Water | To 100 | To 100 |
| Propylene Carbonate | 7.5 | 7.5 |
| 1,3-Propane Diol | 10 | 10 |
| NLC Of Arginine and Soy Protein | 4 | 0 |

D.I. = deionized

Brown Brazilian type III hair tresses are treated with either the formulation of Example 34 containing NLC of arginine and Soy protein or the formulation of Example 35 that does not contain NLC according to the dipping procedure previously described. The soaking time was 30 min. in each example. The thermal treatment protocol was also followed according to the procedure previously described.

A panel sensory testing was conducted according to the procedure previously described comparing the treatment formulation 34 to the treatment formulation 35. The hair tresses treated with formulation 34 that contains NLC of Arginine and Soy protein have a better dry feel (softer and silkier) than the tresses treated with Formulation 35 that does not contains NLC.

The hair tresses treated with the formulation of Example 34 containing NLC of Arginine and Soy protein were easier to comb when wet and dry than the tresses treated with the formulation of Example 35 that did not contain NLC. Both sets of tresses were repeatedly shampooed as previously described in the wash fastness procedure. The tresses were again evaluated by the sensory panel. The results show similar straightening performance after 5 washes for tresses treated with the formulations of Examples 34 and 35. However, the tresses treated with the formulation of Example 34 containing NLC of Arginine and Soy protein showed better dry feel (remaining very soft and silky) and dry combing even after 5 stripping shampoos than the tresses treated with the formulation of Example 35 that did not contain NLC.

What is claimed is:

1. A process for shaping hair fibers comprising;
   a) coating hair fibers with a hair care composition comprising:
   i) propylene carbonate;
   ii) propylene glycol
   iii) pH adjusting agent
   iv) rheology modifier and
   v) a cosmetically acceptable carrier;
   wherein the amount of component i)+component ii) ranges from about 16 to about 35 wt. %, or from about 17 to about 30 wt. %, or from about 18 to about 25 wt. %, based on the total wt. of the composition; and
   wherein the wt. ratio of component i)/component ii) ranges from about 0.3 to about 3.5, or from about 0.5 to about 3.5, or from about 0.6 to about 3, or from about 0.7 to about 2.5, or from about 0.75 to about 2, wherein the hair care composition is devoid of hair dyes; devoid of sulfite, bisulfite, thiol and mercaptan containing moieties; devoid of alkylene carbonates other than propylene carbonate; devoid of imidazolinum compounds, pyrazolinium compounds, pyridinium compounds, pyrimidium compounds, tetra(C1-C6) alkyl phosphonium compounds, tetra(C1-C6) alkylammonium compounds, guanidinium compounds, cholinium compounds, pyrrolidinium compounds, uranium compounds, thiouronium compounds, and isothiouronium compounds; and
   b) permitting the hair care composition to contact the hair fibers for a sufficient soak time for said hair care composition to penetrate the hair fibers wherein the soak time ranges from about 15 minutes to about 60 minutes; and
   c) contacting the coated hair fibers with a heating appliance and mechanically shaping said hair fibers with the heating appliance to a desired configuration wherein said heating appliance is at a temperature ranging from about 150° C. to about 250° C., or from about 175° C. to about 240° C., or about 200° C. to about 235° C., or from about 220° C. to about 230° C.

2. The process of claim 1, wherein said heating appliance in contact with said hair fibers is pulled from the root end of the hair fibers to the tip of the hair fibers to straighten the hair.

3. The process of claim 1, wherein said heating appliance in contact with said hair fibers is pulled from the root end of the hair fibers to the tip of the hair fibers at a glide speed of at least 1 cm/sec, or at least 3 cm/sec, or at least 5 cm/sec, or at least 7 cm/sec, or at least 10 cm/sec.

4. The process of claim 1, wherein said heating appliance in contact with said hair fibers is pulled from the root end of the hair fibers to the tip of the hair fibers at a glide speed ranging from about 1 cm/sec to about 15 cm/sec.

* * * * *